(12) United States Patent
Bidney et al.

(10) Patent No.: US 6,608,240 B1
(45) Date of Patent: Aug. 19, 2003

(54) SUNFLOWER DISEASE RESISTANCE GENES

(75) Inventors: Dennis L. Bidney, Urbandale, IA (US); Xu Hu, Urbandale, IA (US); Guihua Lu, Urbandale, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 141 days.

(21) Appl. No.: 09/602,472

(22) Filed: Jun. 23, 2000

Related U.S. Application Data

(60) Provisional application No. 60/140,876, filed on Jun. 24, 1999.

(51) Int. Cl.[7] .......................... A01H 5/00; A01H 5/10; C12N 5/04; C12N 15/29; C12N 15/82
(52) U.S. Cl. .............. 800/279; 800/301; 800/322; 800/312; 800/306; 800/320.1; 800/526.2; 800/320.3; 435/430; 435/418; 435/419; 435/320.1; 536/236
(58) Field of Search .............. 536/24.5, 23.6; 800/279, 286, 320.1, 322, 320.2, 312, 320.3, 306, 298, 301; 435/468, 412, 415, 416, 418, 419, 320.1

(56) References Cited

FOREIGN PATENT DOCUMENTS

WO  WO 98/13478 A2  4/1998

OTHER PUBLICATIONS

Lazar et al., Transforming Growth Factor x: Mutation of Aspartic Acid 47 and Leucine 48 Results in Different Biological Activities, Mar. 1988, Molecular and Cellular Biology, vol. 8, No. 3, pp. 1247–1252.*

Hill et al., Functional Analysis of Conserved Histidines in ADP–Glucose Pyrophosphorylase from *Escherichia coli*, 1998, Biochemical and Biophysical Research Comm., vol. 244, pp. 573–577.*

Gentzbittel et al. (1998), "Cloning of Molecular Markers for Disease Resistance in Sunflower, *Helianthus annuus* L.," *Theor. Appl. Genet.* 96:519–525.

Ronald, P.C. (1998), "Resistance Gene Evolution," *Current Opinion in Plant Biology* 1:294–298.

* cited by examiner

Primary Examiner—David T. Fox
Assistant Examiner—Anne Kubelik
(74) Attorney, Agent, or Firm—Pioneer Hi-Bred International, Inc.

(57) ABSTRACT

Compositions and methods for enhancing disease resistance in plants are provided. Compositions comprise sunflower resistance gene analogs. The methods involve transforming a plant with a resistance nucleotide sequence. The methods find use in enhancing broad-based resistance in plants to pathogens. Also provided are transformed plants, plant cells, tissues, and seeds having enhanced disease resistance. The R gene analogs can be used as molecular markers for disease resistance.

40 Claims, 6 Drawing Sheets

Figure 1. Multiple Alignment of sunflower PK1A amino acid sequence with other protein kinases.

CLUSTAL W (1.7) multiple sequence alignment

```
PK1A         MG-CFSCFDS-KEDGKSKPQKTRADHNEVHPSAPSNISRLPSGLDRQKSRNNVS----LR
PK1B         MG-CFPCFESSQEDNNFNHQKVG---HEVHPSAPSNISRLSSGVDRMKTRNNVNNAASLR
NAK_ARATH    MGGCFSNRIKTDI------ASSTWLSSKFLSRD-------GSKGSSTASFSYMP-----R
APK1A        MGICLSAQVK---------AESSGASTKYDAKDI------GSLGSKASSVSVRPS---PR
PK_ARATH     MGNCLDSSAKVDSSSHSPHANSASLSSRVSSKTSRSTVPSSLSINSYSSVESLPT---PR
PTO-KINASE   MS-CFSCCDD-DD------MHRATDNGPFMAHNS-----AGNNGGQRATESAQR-----E
             *. *:          .                   . :               .

PK1A         KESSGSKDGSQGQIAAHTFTFRELAAATNNFSPDCLLGEGGFGHVYRGRLP---------
PK1B         RESSGPPD---AQIAAQTFTFRELAAATNNFQPDCFLREGGFGCVYRGRLQ---------
NAK_ARATH    TEGEILQN-----ANLKNFSLSELKSATRNFRPDSVVGEGGFGCVFKGWIDESSLAPSKP
APK1A        TEGEILQS-----PNLKSFSFAELKSATRNFRPDSVLGEGGFGCVFKGWIDEKSLTASRP
PK_ARATH     TEGEILSS-----PNLKAFTFNELKNATRNFRPDSLLGEGGFGYVFKGWIDGTTLTASKP
PTO-KINASE   TQTVNIQP-----IAVPSIAVDELKDITDNFGSKALIGEGSYGRVYHGVLK---------
                :            ::.  **    * **  ....:  **.:* *::* :

PK1A         GSGQIVAVKQLDRNGLQGNREFLVEVLMLSLLHHPNLVNLIGYCADGDQRLLVYEFMPLG
PK1B         SSGQVVAVKQLDRNGLQGNREFLVEVLMLSLLHHPNLVNLIGYCADGDQRLLVYEFMALG
NAK_ARATH    GTGIVIAVKRLNQEGFQGHREWLAEINYLGQLDHPNLVKLIGYCLEEEHRLLVYEFMTRG
APK1A        GTGLVIAVKKLNQDGWQGHQEWLAEVNYLGQFSHRHLVKLIGYCLEDEHRLLVYEFMPRG
PK_ARATH     GSGIVVAVKKLKTEGYQGHKEWLTEVNYLGQLSHPNLVKLVGYCVEGENRLLVYEFMPKG
PTO-KINASE   -SGRAAAIKKLD-SSKQPDREFLAQVSMVSRLKDENVVELLGYCVDGGFRVLAYEYAPNG
              :*   *:*:*.  .. * .:*:*..::  :. : . ::*:*:*** :   *:*.**: . *

PK1A         SLEDHLHDLPPE--KEA---LDWNTRMKIAAGAARGLEFLHDKANPPVIYRDFKSSNILL
PK1B         SLEDHLHDVPPD--REP---LDWTQ-DEDSGCAAKGLEFLHDKANPPVIYRDFKSSNILL
NAK_ARATH    SLENHLFRRGTF--YQP---LSWNTRVRMALGAARGLAFLHN-AQPQVIYRDFKASNILL
APK1A        SLENHLFRRGLY--FQP---LSWKLRLKVALGAAKGLAFLHS-SETRVIYRDFKTSNILL
PK_ARATH     SLENHLFRRG----AQP---LTWAIRMKVAIGAAKGLTFLHD-AKSQVIYRDFKAANILL
PTO-KINASE   SLHDILHGRKGVKGAQPGPVLSWAQRVKIAVGAAKGLEYLHEKAQPHIIHRDIKSSNILL
             **.: *.            :.   *  *    . :  **:** :**.  ::. :*:**::****

PK1A         GEGFQPKLSDFGLAKLGPTGDKSHVSTRVMGTYGYCAPEYAMTGQLTVKSDVYSFGVVFL
PK1B         DEGFQPKLSDFGLAKLGPTGDKSHVSTRVMGTYGYCAPEYAMTGQLTVKSDVYSFGVVFL
NAK_ARATH    DSNYNAKLSDFGLARDGPMGDNSHVSTRVMGTQGYAAPEYLATGHLSVKSDVYSFGVVLL
APK1A        DSEYNAKLSDFGLAKDGPIGDKSHVSTRVMGTHGYAAPEYLATGHLTTKSDVYSFGVVLL
PK_ARATH     DAEFNSKLSDFGLAKAGPTGDKTHVSTQVMGTHGYAAPEYVATGRLTAKSDVYSFGVVLL
PTO-KINASE   FDDDVAKIADFDLSNQAPDMAARLHSTRVLGTFGYHAPEYAMTGQLSSKSDVYSFGVVLL
                .*::**.*:. .*       **:*.** ** ****   **:*:  **********.*

PK1A         ELITGRKAIDSSAPQGQQNLVTWARPLFNDRRKFATLADPRLEGHYPMRGLYQALAVASM
PK1B         ELITGRKAIDSTQPHGQQNLVTWARPLFNDRRKFTSLVDPRLEGRYPMRGLYQALAVASM
NAK_ARATH    ELLSGRRAIDKNQPVVEHNLVDWARPYLTNKRRLLRVMDPRLQGQYSLTRALKIAVLALD
APK1A        ELLSGRRAVDKNRPSGERNLVEWAKPYLVNKRKIFRVIDNRLQDQYSMEEACKVATLSLR
PK_ARATH     ELLSGRRAVDKSKVGMEQSLVDWATPYLGDKRKLFRIMDTRLGGQYPQKGAYTAASLALQ
PTO-KINASE   ELLTGRKPVDHTLPRG--NRVCYLGNARLSEDKVKQCVDARLNTDYPPKAIAKMAAVAAL
             **::**:.:*      .      .  *    ..  :.     *  **    *.          ::

PK1A         CIQEQAAARPLIGDVVTALSYLANHTYDPNAASG-QSNRYNNGERTSRISKNEEGGGSGR
PK1B         CIQEQVAARPLIADVVTALSYLANQGYDPTTAP---SFITSSAAPAARRDLKPQG-----
NAK_ARATH    CISIDAKSRPTMNEIVKTMEELHIQKEAS------KEQQNPQISIDNIINKSPQA-----
APK1A        CLTTEIKLRPNMSEVVSHLEHIQSLNAAIGG-NMDKTDRRMRRRSDSVVSKKVNAGFARQ
PK_ARATH     CLNPDAKLRPKMSEVLAKLDQLESTKPGTGVGNRQAQIDSPRGSNGSIVQKSPRRYSYDR
PTO-KINASE   CVQYEADFRPNMSIVVKLFSLCCLDLYQVR-----HQACEFSPYPCLYVMK---------
             *:   :  **     :  ::      :.

PK1A         SRWGDLEGSDKGDSPRETQTPRMLNRDLDRERAVAEAKMWVEKRRQSAQGSFDGNANG
PK1B         -----FRKTMKGVAADGIWKNRILPKKL--------------------------
NAK_ARATH    ----------VNYPRPSIM--------------------------------
APK1A        T----AVGSTVVAYPRPSASPLYV-----------------------------
PK_ARATH     P----LLHITPGASPLPTHNHSPRVR---------------------------
PTO-KINASE   ---------------------------------------------------
```

Figure 2. Protein Distance Analysis (PHYLIP) of sunflower PK1A and other known protein kinases using Neighbor-Joining/UPGMA method (version 3.572c).

```
      +-------NAK_ARATH
      !
--4---------APK1A
      !
      !                                      +---PK1A
      !                     +--------------1
      !    +-------------2                   +------PK1B
      !    !                !
      +--3                  +---------------------------PTO-KINASE
           !
           +----------PK_ARATH
```

* this is an unrooted tree!

| Between | And       | Length  |
|---------|-----------|---------|
| 4       | NAK_ARATH | 0.55646 |
| 4       | APK1A     | 0.62247 |
| 4       | 3         | 0.15408 |
| 3       | 2         | 0.90833 |
| 2       | 1         | 0.97900 |
| 1       | PK1A      | 0.27888 |
| 1       | PK1B      | 0.46034 |
| 2       | PTO-KINASE| 2.08455 |
| 3       | PK_ARATH  | 0.74085 |

Figure 3. Alignment of the deduced amino acid sequences of two sunflower NBS-LRR contigs with that of the disease-resistance genes of tobacco N, flax M (rust), and Arabidopsis RPP5 and RPS2 using the CLUSTAL W method.

Multiple Alignment:

```
CLUSTAL W (1.7) multiple sequence alignment

RS6-8con        GVGGGGKTTLASAAY------MEISHLFEGCCLLENIREES-SKQGLKKLQENFLSLVLK
RS7-4con        GVGGGGKTTLASAAY------AEISRRFEAHCLLQNIREES-NKHGLEKLQEKILSLVLK
N_gene          GMGGVGKTTIARAIFDTLLGRMDSSYQFDGACFLKDIKE---NKRGMHSLQNALLSELLR
Rust            GMGGIGKTTTAKAVY------NKISSHFDRCCFVDNVRAMQEQKDGIFILQKKLVSEILR
RPS5            GMAGIGKTTLARAAY------DQLSRDFEASCFIEDFDR--------EFQEKGFFGLLEK
RPS2            GPGGVGKTTLMQSINN---ELITKGHQYDVLIWVQMSRE-----FGECTIQQAVGARLGL
                 * * ****       :         . ::   :.        :: . . :

RS6-8con        T-DVKVGNEIIGRSMIKSRLSHKRFLVVLDDVDN-FEQLEALAGSHDWFGEGSRIIITTR
RS7-4con        TKDVVVGSEIEGRSMIERRLRNKSVLVVLDDVDD-LKQLEALAGSHAWFGKGSRIIITTR
N_gene          E-KANYNNEEDGKHQMASRLRSKKVLIVLDDIDNKDHYLEYLAGDLDWFGNGSRIIITTR
Rust            MDSVGFTNDSGGRKMIKERVSKSKILVVLDDVDE-KFKFEDILGCPKDFDSGTRFIITSR
RPS5            Q--LGVNPQVTRLSILLKTLRSKRILLVLDDVRK-PLGATSFLCEFDWLGPGSLIIVTSQ
RPS2            SWDEKETGENR-ALKIYRALRQKRFLLLLDDVWEEIDLEKTGVPRPDRENK-CKVMFTTR
                    :        :    . . .*::***: .        .    .:.*::

RS6-8con        DVHLLSS---RAQTIYEVNLLSQDEAIKLLKRYAYHKDKP-VEEYEMLAEEVVSYAGGLP
RS7-4con        DEHLLTR---HADMIYEVSLLSHDEAMELFNKHAYRKDKP-IEDYEMLSNDVVSYASGLP
N_gene          DKHLIE----KNDIIYEVTALPDHESIQLFKQHAFGKEVP-NENFEKLSLEVVNYAKGLP
Rust            NQNVLSRLNENQCKLYEVGSMSEQHSLELFSKHAFKKNTP-PSDYETLANDIVSTTGGLP
RPS5            DKQVLVQ--CQVNEIYKVQGLNKHESLQLFSRCAFGKDVP-DQNLLELSMKFVDYANGNP
RPS2            SIALCNN--MGAEYKLRVEFLEKKHAWELFCSKVWRKDLLESSSIRRLAEIIVSKCGGLP
                . :             .*  :  ...: :*:    .: *:     *:  .*.  * *

RS6-8con        LALKV
RS7-4con        LALE-
N_gene          LALKV
Rust            LTLKV
RPS5            LALSI
RPS2            LALIT
                * : *
```

Figure 4. Sequence comparison between RS6-8 contig and TMV tobacco resistance protein N:

Multiple Alignment:

```
CLUSTAL W (1.7) multiple sequence alignment

RS6-8contig     ----------------------------------------------------------
A54810_N_gene_  MASSSSSSRWSYDVFLSFRGEDTRKTFTSHLYEVLNDKGIKTFQDDKRLEYGATIPGELC RS6-8contig     ----------------------------------------------------------
A54810_N_gene_  KAIEESQFAIVVFSENYATSRWCLNELVKIMECKTRFKQTVIPIFYDVDPSHVRNQKESF RS6-8contig     ----------------------------------------------------------
A54810_N_gene_  AKAFEEHETKYKDDVEGIQRWRIALNEAANLKGSCDNRDKTDADCIRQIVDQISSKLCKI RS6-8contig     ---------------------------------------------------------MEIS
A54810_N_gene_  SLSYLQNIVGIDTHLEKIESLLEIGINGVRIMGIWGMGGVGKTTIARAIFDTLLGRMDSS
                                                                         *: *

RS6-8contig     HLFEGCCLLENIREESSKQGLKKLQENFLSLVLKTDVKVGNEIIGRSMIKSRLSHKRFLV
A54810_N_gene_  YQFDGACFLKDIKE--NKRGMHSLQNALLSELLREKANYNNEEDGKHQMASRLRSKKVLI
                  : *:*.*:*:*  .*:*:,.**: :** :*:  ..: .** *:  : *** *:.*:

RS6-8contig     VLDDVDN-FEQLEALAGSHDWFGEGSRIIITTRDVHLLSSRAQTIYEVNLLSQDEAIKLL
A54810_N_gene_  VLDDIDNKDHYLEYLAGDLDWFGNGSRIIITTRDKHLIE-KNDIIYEVTALPDHESIQLF
                ****:**   ** ***. ****:********** **:. : : ****. *.:.*:*:*:

RS6-8contig     KRYAYHKDKPVEEYEMLAEEVVSYAGGLPLALKVLGSFLYGKDKDEWKSTLAKLKCIPEE
A54810_N_gene_  KQHAFGKEVPNENFEKLSLEVVNYAKGLPLALKVWGSLLHNLRLTEWKSAIEHMKNNSYS
                *::*: *:  * *:* *: ***.** ******* **:*:.    ****:: ::*  . .

RS6-8contig     KVMERLKISYDGLEPYQKELFLDIACFMRRWWLQSVLDRAMMVLDACNLHPVIGLKVLEQ
A54810_N_gene_  GIIDKLKISYDGLEPKQQEMFLDIACFLR--GEE--KDYILQILESCHIGAEYGLRILID
                 ::::********** *:*:*******:*        *  : :*::*::  . **::* :

RS6-8contig     KSLIKVSKKGRFEMHDLIEEMAHYIVRGEHPNNPEKHSRIWNREDLEELCAMGAAAPSME
A54810_N_gene_  KSLVFISEYNQVQMHDLIQDMGKYIVNFQK--DPGERSRLWLAKEVEEVMSNNTGTMAME
                ***:  :*:   .::******:*:.***. ::   :*  ::**:*  :::.: :**

RS6-8contig     NEVLANLP--------------MYIISHPGLLLDVVPNMKNLRWIMLIGHGDPSSSFPS
A54810_N_gene_  AIWVSSYSSTLRFSNQAVKNMKRLRVFNMGRSSTHYAIDYLPNNLRCFVCTNYPWESFPS
                 ::. .                  : ::         . .     ::   . * .****

RS6-8contig     NFQPTKLRCLMLIESKQKELWEGCKSLPNLKILDLSGSSNLIKTPDFEGLPCLERLILKY
A54810_N_gene_  TFELKMLVHLQLRHNSLRHLWTETKHLPSLRRIDLSWSKRLTRTPDFTGMPNLEYVNLYQ
                .*: . *  * *  ... :.**   * **.*: :*** *..* :**** *:* **  : *

RS6-8contig     CERLEEIHPSIGYHKRLVYVNMKGCARLKRFPPIIHMKKLETLNLSDCSKLQQFPDIQSN
A54810_N_gene_  CSNLEEVHHSLGCCSKVIGLYLNDCKSLKRFP-CVNVESLEYLGLRSCDSLEKLPEIYGR
                *..***:* *:*  .::: : ::.* *****  :  ::.** *.* .*..*::*:*  ..

RS6-8contig     MDSLVTIDLHNTGIEIIPPSVGRFCTNLVSLDLSQCYKLKRIEDSFHLLKSLKDLNLSCC
A54810_N_gene_  MKPEIQIHMQGSGIRELPSSIFQYKTHVTKLLLWNMKNLVALPSSICRLKSLVSLSVSGC
                *.. :  *.::.:**. :*.*:  :: *:..* * :   :*   .*: **** .*.:* *

RS6-8contig     FGLQSFRQDR------------LVSLKLP---------------------QFP----
A54810_N_gene_  SKLESLPEEIGDLDNLRVFDASDTLILRPPSSIIRLNKLIILMFRGFKDGVHFEFPPVAE
                  *:*: ::              : *: *                        :**
```

```
RS6-8contig      --RFLRKLNLRGCRLEDGGIPSDIF-------------------------------
A54810_N_gene_   GLHSLEYLNLSYCNLIDGGLPEEIGSLSSLKKLDLSRNNFEHLPSSIAQLGALQSLDLKD
                   : *. ***   *.*  ***:*.:*

RS6-8contig      ------------------------------------------------------------
A54810_N_gene_   CQRLTQLPELPPELNELHVDCHMALKFIHYLVTKRKKLHRVKLDDAHNDTMYNLFAYTMF RS6-8contig      ------------------------------------------------------------
A54810_N_gene_   QNISSMRHDISASDSLSLTVFTGQPYPEKIPSWFHHQGWDSSVSVNLPENWYIPDKFLGF RS6-8contig      ------------------------------------------------------------
A54810_N_gene_   AVCYSRSLIDTTAHLIPVCDDKMSRMTQKLALSECDTESSNYSEWDIHFFFVPFAGLWDT RS6-8contig      ------------------------------------------------------------
A54810_N_gene_   SKANGKTPNDYGIIRLSFSGEEKMYGLRLLYKEGPEVNALLQMRENSNEPTEHSTGIRRT RS6-8contig      ---------------
A54810_N_gene_   QYNNRTSFYELING
```

Figure 4A

SUNFLOWER DISEASE RESISTANCE GENES

CROSS-REFERENCE TO RELATED APPLICATION

This application claims the benefit of U.S. Provisional Application No. 60/140,876, filed Jun. 24, 1999.

FIELD OF THE INVENTION

The invention relates to the genetic manipulation of plants, particularly to transforming plants with genes that enhance disease resistance, and breeding program for screening tolerance/resistance lines.

BACKGROUND OF THE INVENTION

Disease in plants is caused by biotic and abiotic causes. Biotic causes include fungi, viruses, bacteria, and nematodes. Of these, fungi are the most frequent causative agent of disease on plants. Abiotic causes of disease in plants include extremes of temperature, water, oxygen, soil pH, plus nutrient-element deficiencies and imbalances, excess heavy metals, and air pollution.

A host of cellular processes enables plants to defend themselves from disease caused by pathogenic agents. These processes apparently form an integrated set of resistance mechanisms that is activated by initial infection and then limits further spread of the invading pathogenic microorganism.

Subsequent to recognition of a potentially pathogenic microbe, plants can activate an array of biochemical responses. Generally, the plant responds by inducing several local responses in the cells immediately surrounding the infection site. The most common resistance response observed in both non-host and race-specific interactions is termed the "hypersensitive response" (HR). In the hypersensitive response, cells contacted by the pathogen, and often neighboring cells, rapidly collapse and dry in a necrotic fleck. Other responses include the deposition of callose, the physical thickening of cell walls by lignification, and the synthesis of various antibiotic small molecules and proteins. Genetic factors in both the host and the pathogen determine the specificity of these local responses, which can be very effective in limiting the spread of infection.

The hypersensitive response in many plant-pathogen interactions results from the expression of a resistance (R) gene in the plant and a corresponding avirulence (avr) gene in the pathogen. (Flor (1971) *Ann. Rev. Phytopath.* 9:274). This interaction is associated with the rapid, localized cell death of the hypersensitive response. R genes that respond to specific bacterial, fungal, or viral pathogens, have been isolated from a variety of plant species and several appear to encode cytoplasmic proteins.

The resistance gene in the plant and the avirulence gene in the pathogen often conform to a gene-for-gene relationship. That is, resistance to a pathogen is only observed when the pathogen carries a specific avirulence gene and the plant carries a corresponding or complementing resistance gene. The theory has been developed by genetic studies of plant/pathogen interactions in a variety of plant systems (Keen (1990) *Ann. Rev. Genet.* 24:447–463). Because avrR gene-for-gene relationships are observed in many plant-pathogen systems and are accompanied by a characteristic set of defense responses, a common molecular mechanism underlying avrR gene mediated resistance has been postulated. A simple model which has been proposed is that pathogen avr genes directly or indirectly generate a specific molecular signal (ligand) that is recognized by cognate receptors encoded by plant R genes.

Both plant resistance genes and corresponding pathogen avirulence genes have been cloned. The plant kingdom contains thousands of R genes with specific specificities for viral, bacterial, fungal, or nematode pathogens. Although there are differences in the defense responses induced during different plant-pathogen interactions, some common themes are apparent among R gene-mediated defenses. The function of a given R gene is dependent on the genotype of the pathogen. Plant pathogens produce a diversity of potential signals, and in a fashion analogous to the production of antigens by mammalian pathogens, some of these signals are detectable by some plants.

Recently a number of R genes have been isolated from various plant species that interact with different pathogens (avr) genes (Bent (1996) *Plant Cell* 8:1757–1771; Hammond-Kosack et al. (1997) *Ann. Rev. Plant Physiol. Plant Mol. Biol.* 48:575–607; Ellis et al. (1988) *Cur. Opin. in Plant Path.* 1:288–293). The recent development of new methods for gene isolation in plants has permitted isolation of many R genes from other plant species (Yu et al. (1996) *Proc. Natl. Acad. Sci. USA* 93:11751–11756; Leister et al. (1998) *Proc. Natl. Acad. Sci. USA.* 95:370–375). Although the products of most avirulence genes show very little homology with each other, the reported R genes have conserved functional domains such as the protein kinase (PK) domain, leucine-rich regions (LRR), nucleotide-binding sites (NBS) Bent (1996) *Plant Cell* 8:1757–1771; Ellis et al. (1988) *Cur. Opin. in Plant Path.* 1:288–293).

The R genes can be classified into four main classes based on the structure of R gene products (Bent (1996) *Plant Cell* 8:1757–1771; Ellis et al. (1988) *Cur. Opin. in Plant Path.* 1:288–293; Hammond-Kosack et al. (1997) *Ann. Rev. Plant Physiol. Plant Mol. Biol.* 48:575–607; NBS-LRR (nucleotide-binding site-Leucine-rich repeat), LRR-TM-PK (Leucine-rich repeat-transmembrane domain-protein kinase), LRR-TM (Leucine-rich repeat-transmembrane domain), and PK (protein kinase). The largest number of characterized R proteins is the NBS-LRR type. These group genes can be recognized into two subgroups by the presence or absence of an amino-terminal region (TIR domain). TIR domain has sequence and structural similarity to the cytoplasmic signaling domains of Toll and interleukin-1 receptor (Baker et al. (1997) *Science* 276:726–733; Parker et al. (1997) *Plant Cell* 9:879–894).

The first subgroup includes tobacco TMV N gene, Hammond-Kosack et al. (1997) *Ann. Rev. Plant Physiol. Plant Mol. Biol.* 48:575–607, L6 (flax rust resistance), Hammond-Kosack et al. (1997) *Ann. Rev. Plant Physiol. Plant Mol. Biol.* 48:575–607, and RPP5 (downy mildew resistance), Parker et al. (1997) *Plant Cell* 9:879–894. The second subgroup without TIR domain includes RPS2, RPM1 Hammond-Kosack et al. (1997) *Ann. Rev. Plant Physiol. Plant Mol. Biol.* 48:575–607, and Prf Salmeron et al. (1996) *Cell* 86:123–133. These three R genes contain an amino-terminal leucine zipper (LZ) domain. The LZ domain may involve in protein-protein interaction in the signaling pathways. The proteins in these two subclasses signal through different pathways. Proteins in the TIR class signal via a pathway that includes EDS1 (Parker et al. (1996) *Plant Cell* 8:2033–2046) whereas the other class signals through a pathway that includes NDR1 gene (Centry et al. (1997) *Science* 278:1963–1965). The function of NBS may relate to HR and evidence has shown that NBS of RPS2 binds nucleotide (Ellis et al. (1988) *Curr. Opin. in Plant Path.*

1:288–293). Many NBS-LRR plant genes have been identified through plant genome sequencing projects (Botella et al. (1997) *Plant J*. 12:1197–1121), and by PCR using degenerate primers based on the NBS motifs. Yu et al. (1996) *Proc. Natl. Acad Sci. USA* 93:11751–11756; Leister et al. (1998) *Proc. Natl. Acad. Sci. USA*. 95:370–375.

Both LRR-TM-PK and PK classes of R genes contain kinase domain. Ligand binding activates the protein kinase domain. The first receptor-like protein kinase (RLK) gene is maize ZmPK1 that was isolated using degenerate primers to the kinase domain (Walker et al. (1990) *Nature* 345:743–746). Since then, a number of RLKs have been isolated from plants. The plant RLKs belongs to serine/threonine kinase family except ZmPK1. All of the plant RLKs can be classified according to the features of the predicted extracellular domain and transmambrane domain, such as LRR and TM. The function of kinase in defense signaling pathways has been dissected in the Pto/AvrPto interactions (Oldroyd et al. (1988) *Proc. Natl. Acad. Sci. USA* 95:10300–10305; Martin et al. (1996) *Molecular Aspects of Pathogenicity and Resistance: Requirement for Signal Transduction*, (pages 163–186). In the signal transduction, Pto, together with Prf, is required for the hypersensitive response induction after AvrPto perception. Pto also interacts with a family of transcriptional factors- Pti4, Pti5, and Pti6- that binds to a conserved cis-element present in promoter region of many genes encoding PR proteins (Zhou et al. (1997) *EMBO J*. 16:3207–3218). Expression of PR proteins is specifically enhanced upon Pto-Avrpto recognition in transgenic tobacco proteins (Zhou et al. (1997) *EMBO J*. 16:3207–3218).

In general, an R gene provides resistance against only some strains of a particular pathogen species. However, it has been demonstrated that R genes can be functional in heterologous systems (Thilmony et al. (1995) *Plant Cell* 7:1529–1536; Parker et al. (1996) *Plant Cell* 8:2033–2046). Furthermore, overexpression of R gene Prf activates pathways in a pathogen-independent manner and leads to the activation of systemic acquired resistance (SAR). The transgene-induced SAR has implications for the generation of broad-spectrum disease resistance in agricultural crop plants (Oldroyd et al. (1988) *Proc. Natl. Acad. Sci. USA* 95:10300–10305). One example of a strain-nonspecific resistance gene, mlo, has been cloned (Buschges et al. (1997) *Cell* 88:695–705).

As noted, among the causative agents of infectious disease of crop plants, the phytopathogenic fungi play the dominant role. Phytopathogenic fungi cause devastating epidemics, as well as causing significant annual crop yield losses. All of the approximately 300,000 species of flowering plants are attacked by pathogenic fungi. However, a single plant species can be host to only a few fungal species, and similarly, most fungi usually have a limited host range.

Plant disease outbreaks have resulted in catastrophic crop failures that have triggered famines and caused major social change. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight. Accordingly, molecular methods are needed to supplement traditional breeding methods to protect plants from pathogen attack.

SUMMARY OF THE INVENTION

Compositions and methods for creating or enhancing resistance to plant pests in a plant are provided. Compositions of the invention comprise novel disease resistance analogs from sunflower and variants of such resistance genes. The methods involve stably transforming a plant with nucleotide sequences of the invention operably linked with a promoter capable of driving expression of a gene in a plant cell. The sunflower R gene analogs and variants thereof may be used to modulate expression of the resistance gene analogs in plants and to engineer plants with broad-spectrum disease resistance. The methods of the invention find use in controlling plant pests, including fungal pathogens, viruses, nematodes, insects, and the like.

The compositions of the invention are additionally useful as genetic markers. Such genes can be used to facilitate the sunflower breeding programs for disease resistance.

Transformed plants and seeds, as well as methods for making such plants and seeds are additionally provided.

BRIEF DESCRIPTION OF THE DRAWINGS

FIG. 1: Multiple Alignment of PK1A (SEQ ID NO: 2) and PK1B (SEQ ID NO: 4) amino acid sequence with other protein kinases. Other PK proteins included: A protein kinase, NAK_ARATH from Arabidopsis (S38326) (SEQ ID NO: 57); APK1A is another protein kinase from Arabidopsis (D12522) (SEQ ID NO: 58); PK_ARATH is a protein kinase from Arabidopsis (D88207) (SEQ ID NO: 59); PTO-KINASE is a pto like protein kinase from tomato (U28007) (SEQ ID NO: 60).

FIG. 2: Protein Distance Analysis (PHYLIP) of sunflower PK1A, PK1B and other known protein kinases using Neighbor-Joining/UPGMA method (version 3.572c).

FIG. 3: Alignment of the deduced amino acid sequences of two sunflower NBS-LRR contigs (SEQ ID NO: 8, amino acids 1 through 157 and SEQ ID NO: 13, amino acids 285 through 456) with that of the disease-resistance genes of tobacco N (SEQ ID NO: 61), flax M (rust) (SEQ ID NO: 62), and arabidopsis RPP5 (SEQ ID NO: 63) and RPS2 (SEQ ID NO: 64) using the CLUSTAL W method.

FIG. 4: Sequence comparison between RS6-8 contig (SEQ ID NO: 8) and TMV tobacco resistance protein N (SEQ ID NO: 61).

DETAILED DESCRIPTION OF THE INVENTION

Figure 5:
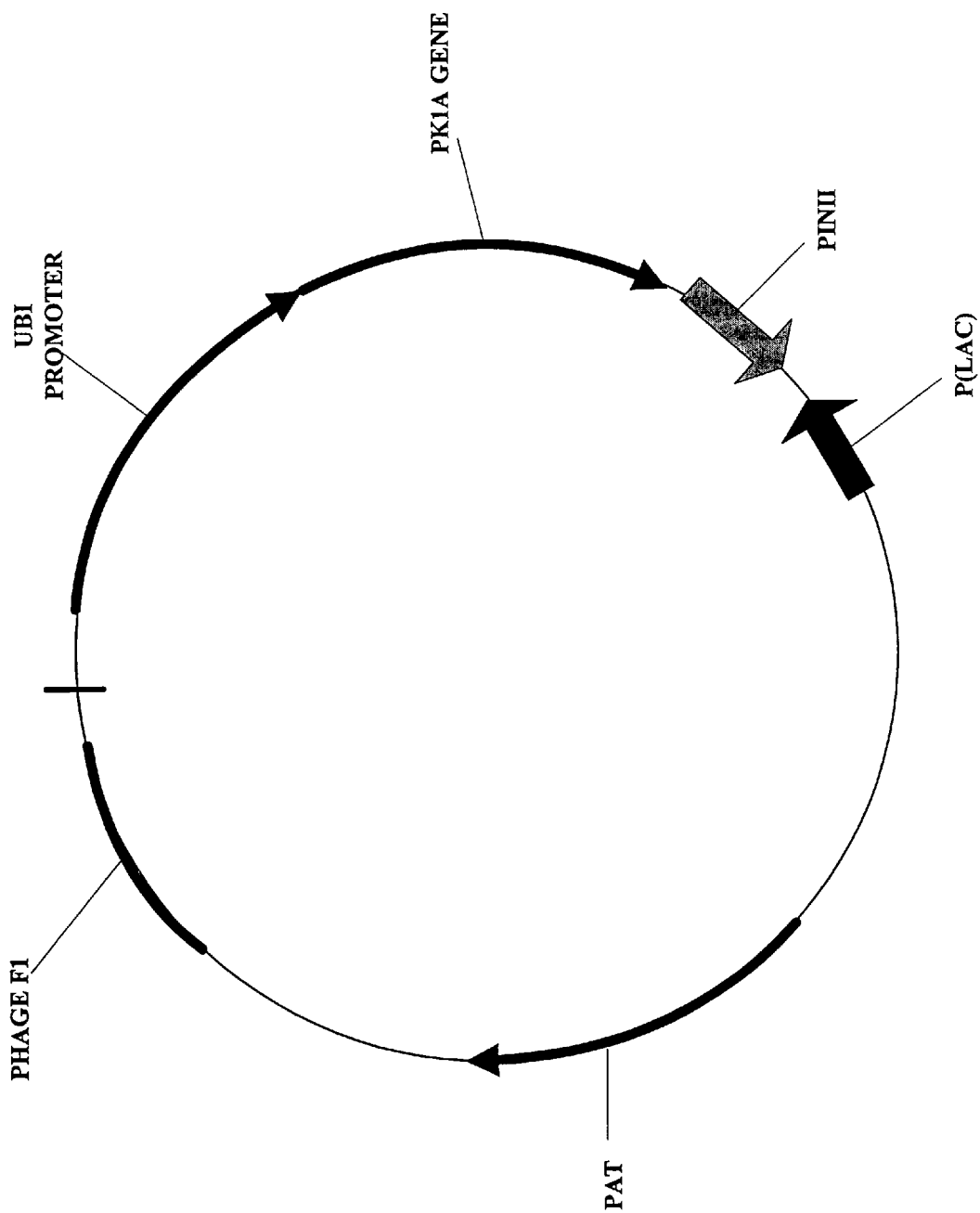
FIG. 5: Example of an expression vector containing R gene operably linked to a UBI promoter.

The invention is drawn to methods for creating or enhancing resistance in a plant to plant pests. Accordingly, the methods are also useful in protecting plants against fungal pathogens, viruses, nematodes, insects and the like.

The R genes of the invention can be used as markers in genetic mapping as well as in assessing disease resistance in a plant of interest. Thus, the sequences can be used in breeding programs. See, for example, Gentzbittel et al. (1998) *Theor. Appl. Genet*. 96:519–523.

Additional uses for the sequences of the invention include using the sequences as bait to isolate other signaling components on defense/resistance pathways and to isolate the corresponding promoter sequences. The sequences may also be used to modulate plant development processes, such as pollen development, regulation of organ shape, differentiation of aleurone and shoot epidermis, embryogenic competence, and cell/cell interactions. See, generally, Sambrook et al. (1989) *Molecular Cloning: A Laboratory Manual* (2nd ed., Cold Spring Harbor Laboratory Press, Plainview, N.Y.).

Methods for creating or enhancing disease resistance in a plant are provided. The methods involve stably transforming a plant with a DNA construct comprising an sunflower R nucleotide sequence of the invention operably linked to promoter that drives expression in a plant. Such methods find use in agriculture particularly in limiting the impact of plant pathogens on crop plants. The sunflower R nucleotide sequences are selected from nucleotide sequences encoding sunflower R proteins. Preferably, such sunflower R proteins encode protein kinases (PK) and nucleotide binding site-leucine rich repeat-type proteins (NBS-LRR). More preferably, such sunflower R proteins are selected from the proteins whose amino acid sequences are set forth in SEQ ID NOs: 2, 4, and 8 and the proteins encoded by the nucleotide sequences set forth in SEQ ID NOs: 1, 3, 5, 6, 7, 10–13, and 14. While the choice of promoter will depend on the desired timing and location of expression of the antipathogenic nucleotides sequences, specific promoters include pathogen-inducible promoters.

By "disease resistance" is intended that the plants avoid or suppress the disease symptoms that are the outcome of plant-pathogen interaction. That is, pathogens are prevented from causing plant diseases and the associated disease symptoms. The methods of the invention can be utilized to protect plants from disease, particularly those diseases that are caused by plant pathogens, such as broomrape, sclerotina, downey mildew, etc.

The resistance gene (R) analogs of the invention share homology to disease resistance genes from other plants, including TMV resistance gene N, rust resistance Gene M, downy mildew resistance gene, receptor-like protein kinase, and protein kinase. The R genes of the invention have conserved functional domains such as the protein kinase (PK) domain, leucine-rich regions (LRR), nucleotide-binding sites (NBS). Thus, the genes find use in engineering plants for broad-spectrum disease resistance.

Compositions of the invention comprise sunflower R nucleotides. By "sunflower R nucleotides," is intended coding and antisense sequences for sunflower resistance genes as well as fragments and variants thereof. Nucleotide sequences encoding sunflower resistance proteins are provided in SEQ ID NOs: 1, 3, 5, 6, 7, 10–13, and 14. Alignment of the sequences with other protein kinases are provided in FIGS. 1 and 2. Four sequences having a protein kinase domain are provided; PK1A (SEQ ID NO: 1), PK1B (SEQ ID NO: 3), PK4 (SEQ ID NO: 5) and PK5 (SEQ ID NO: 6). Amino acid sequences for PK1A and PK1B are also provided (SEQ ID NOs: 2 and 4). Six NBS-LRR type analog sequences RS6-8, RAS4-5, RS7-4, RAS5-1, RS6-8 and RS7-4 are provided in SEQ ID NOs: 7, 9–12, and 14, respectively.

Protein kinases play critical roles in regulating of biochemical changes associated with cellular growth. Thus, the sequences of the invention may find use in modulating (decreasing or increasing cellular growth and/or metabolism. The proteins of the invention may be useful for modulating phosphorylation states of molecules.

Compositions of the invention include isolated nucleic acid molecules comprising nucleotide sequences encoding the DNA sequence shown in the sequence listings, or the nucleotide sequence encoding the DNA sequence deposited in a bacteria host, that are involved in modulating cellular growth and/or metabolism. In particular, the present invention provides for isolated nucleic acid molecules comprising nucleotide sequences encoding the amino acid sequences shown in the sequence listing, or the nucleotide sequences encoding the DNA sequences deposited in a bacterial host as Patent Deposit Nos. PTA-139, PTA-140, PTA-141, PTA-142, PTA-135, PTA-137, PTA-136, and PTA-138, and fragments and variants thereof. Further provided are polypeptides having an amino acid sequence encoded by a nucleic acid molecule described herein, for example those set forth in the sequence listings, or those deposited in a bacterial host as Patent Deposit Nos. PTA-139, PTA-140, PTA-141, PTA-142, PTA-135, PTA-137, PTA-136, and PTA-138, and fragments and variants thereof.

Plasmids containing the nucleotide sequences of the invention were deposited with the Patent Depository of the American Type Culture Collection (ATCC), Manassas, Va., on May 26, 2000. The following plasmids were deposited: pHp 15541 containing PK1A, pHp 15542 containing PK1B, pHp 15543 containing PK4, pHp15544 containing PK5, pHp 15537 containing RS6-8, pHp 15539 containing RAS4-5, pHp 15538 containing 7-4, pHp 15540 containing RAS5-1, and assigned Patent Deposit Nos. PTA-139, PTA-140, PTA-141, PTA-142, PTA-135, PTA-137, PTA-136, and PTA-138, respectively. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

Thus, the invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence modulate or regulate gene activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of an R nucleotide sequence that encodes a biologically active portion of an R protein of the invention will encode at least 15, 25, 30, 50, 100, 150, 200, 250, 300, 350, or 400 contiguous amino acids, or up to the total number of amino acids present in a full-length R protein of the invention (for example, 457, 413, 571, or 476 amino acids for SEQ ID NO: 2, 4, 8, or 13, respectively). Fragments of an R nucleotide sequence that are useful as hybridization probes or PCR primers generally need not encode a biologically active portion of an R protein.

Thus, a fragment of an R nucleotide sequence may encode a biologically active portion of an R protein, or it may be a fragment that can be used as a hybridization probe or PCR primer using methods disclosed below. A biologically active portion of an R protein can be prepared by isolating a portion of one of the R nucleotide sequences of the invention, expressing the encoded portion of the R protein (e.g., by recombinant expression in vitro), and assessing the activity of the encoded portion of the R protein. Nucleic acid molecules that are fragments of an R nucleotide sequence comprise at least 16, 20, 50, 75, 100, 150, 200, 250, 300, 350, 400, 450, 500, 550, 600, or 650 nucleotides, or up to the number of nucleotides present in a full-length R nucleotide sequence disclosed herein (for example, 1593, 1559, 2114, 850, 2594, 2793, 670, 1200, 3450, or 1360 nucleotides for SEQ ID NO[s]: 1, 3, 4, 5, 6, 7, 9, 10, 11, 12, or 14, respectively).

By "variants" is intended substantially similar sequences. For nucleotide sequences, conservative variants include those sequences that, because of the degeneracy of the genetic code, encode the amino acid sequence of one of the R polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode an R protein of the invention. Generally, variants of a particular nucleotide sequence of the invention will have at least 50%, 55%, 60%, 65%, 70%, generally at least 75%, 80%, 85%, preferably about 90% to 95% or more, and more preferably about 98% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, modulating or regulatory activity as described herein. Such variants may result from, for example, genetic polymorphism or from human manipulation. Biologically active variants of a native R protein of the invention will have at least 40%, 50%, 60%, 70%, generally at least 75%, 80%, 85%, preferably about 90% to 95% or more, and more preferably about 98% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the R proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired modulating or regulatory activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequence encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by its effect on the plant defense system. See, for example U.S. Pat. No. 5,614,395, herein incorporated by reference.

Variant nucleotide sequences and proteins also encompass sequences and proteins derived from a mutagenic and recombinogenic procedure such as DNA shuffling. With such a procedure, one or more different R coding sequences can be manipulated to create a new R sequence possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the R gene of the invention and other known R genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458. Alternatively, variants may have been manipulated to lose biological activity. Such variants can be made by site directed mutagenesis and the like.

In this manner, the present invention encompasses the R genes and proteins as well as components and fragments thereof. That is, it is recognized that component polypeptides or fragments of the proteins may be produced which retain activity. These fragments include truncated sequences, as well as N-terminal, C-terminal, internal and internally deleted amino acid sequences of the proteins.

It is recognized that with these nucleotide sequences, antisense constructions, complementary to at least a portion of the messenger RNA (mRNA) for the R genes or a regulatory flanking sequences can be constructed. Antisense nucleotides are constructed to hybridize with the corresponding mRNA. Therefore, modifications of the sequences may be made as long as the sequences hybridize to and interfere with expression of the corresponding mRNA. In this manner, antisense constructions having 70%, preferably 80%, more preferably 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the invention can be used to isolate corresponding sequences from other organisms, particularly other plants. Methods are readily available in the art for the hybridization of nucleic acid sequences. Coding sequences from other plants may be isolated according to well known techniques based on their sequence homology to the coding sequences set forth herein. In these techniques all or part of the known coding sequence is used as a probe which selectively hybridizes to other R coding sequences present in a population of cloned genomic DNA fragments or cDNA fragments (i.e. genomic or cDNA libraries) from a chosen organism.

In this manner, methods such as PCR, hybridization, and the like can be used to identify such sequences based on their sequence homology to the sequences set forth herein. Sequences isolated based on their sequence identity to the entire R sequence set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences have a high percentage of sequence identity and/or similarity. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the R sequence of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire R sequence disclosed herein, or one or more portions thereof, may be used as a probe capable of specifically hybridizing to corresponding R sequences and messenger RNAs. To achieve specific hybridization under a variety of conditions, such probes include sequences that are unique among R sequences and are preferably at least about 10 nucleotides in length, and most preferably at least about 20 nucleotides in length. Such probes may be used to amplify corresponding R sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m=81.5°$ C.+16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for an R protein and which hybridize under stringent conditions to the R sequence disclosed herein, or to fragments thereof, are encompassed by the present invention. Such sequences will be at least 50% to 55% homologous, about 60%, 65%, to 70% homologous, and even about 75%, 80%, 85%, 90%, 95% to 98% homologous or more with the disclosed sequence. That is, the sequence identity of sequences may range, sharing at least 50 % to 55%, about 60%, 65% to 70%, and even about 75%, 80%, 85%, 90%, 95% to 98% or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The invention is drawn to compositions and methods for inducing resistance in a plant to plant pests. Accordingly, the compositions and methods are also useful in protecting plants against fungal pathogens, viruses, nematodes, insects and the like.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened. The methods of the invention can be utilized to protect plants from disease, particularly those diseases that are caused by plant pathogens.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium roltsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: *Plasmophora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophominaphaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride*, Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora, Corn stunt spiroplasma, Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.

Nematodes include parasitic nematodes such as root-knot, cyst, and lesion nematodes, including Heterodera and Globodera spp; particularly *Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode).

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; Melanotus spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; Delia ssp., Root maggots.

The R sequences or antisense R sequences of the invention can be introduced into any plant in accordance with the methods disclosed herein to enhance or create resistance to plant pests. The sequences to be introduced may be used in expression cassettes for expression in any plant of interest where expression in the plant cell is necessary for description. In other instances, such as for description or recombination, oligonucleotides are synthesized, purified and introduced into the plant cell.

The R sequences of the invention are provided in expression cassettes for expression in the plant of interest. The cassette will include 5' and 3' regulatory sequences operably linked to an R sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be co-transformed into the organism. Alternatively, the additional gene(s) can be provided on multiple expression cassettes.

Such an expression cassette is provided with a plurality of restriction sites for insertion of the R sequence to be under the transcriptional regulation of the regulatory regions. The expression cassette may additionally contain selectable marker genes.

The expression cassette will include in the 5'–3' direction of transcription, a transcriptional and translational initiation region, an R sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

A number of promoters can be used in the practice of the invention. The promoters can be selected based on the desired outcome. For example, constitutive, inducible, particularly pathogen-inducible, or tissue specific promoters may be used. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *The Plant Cell* 4:645–656; and Van Loon (1985) *Plant Mol. Virol.* 4:111–116.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Molecular and General Genetics* 2:93–98; and Yang, Y (1996) *Proc. Natl. Acad. Sci. USA* 93:14972–14977. See also, Chen et al. (1996) *Plant J.* 10:955–966; Zhang and Sing (1994) *Proc. Natl. Acad. Sci. USA* 91:2507–2511; Warner et al. (1993) *Plant J.* 3:191–201; Siebertz et al. (1989) *Plant Cell* 1:961–968; and the references cited therein. Of particular interest is the inducible promoter for the maize PRms gene, whose expression is induced by the pathogen *Fusarium moniliforme* (see, for example, Cordero et al. (1992) *Physiological and Molecular Plant Pathology* 41:189–200).

Constitutive promoters include, for example, the core promoter of the Rsyn7 promoter and other constitutive promoters disclosed in WO 99/43838, the 35S promoter, the core 35S promoter, and the like. Other constitutive promoters include, for example, U.S. Pat. Nos. 5,608,149; 5,608,144; 5,604,121; 5,569,597; 5,466,785; 5,399,680; 5,268,463; 5,608,142. see also, co-pending application entitled "Constitutive Maize Promoters, application Ser. No. 09/257,584 filed Feb. 25, 1999, and herein incorporated by reference.

Tissue specific promoters include those described in Yamamoto et al. (1997) *Plant J.* 12(2):255–265; Kawamata et al. (1997) *Plant Cell Physiol.* 38(7):792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell. Differ.* 20:181–196; Orozco et al. (1993) *Plant Mol. Biol.* 23(6):1129–1138; Matsuoka et al. (1993) *Proc. Natl. Acad. Sci. U.S.A.* 90(20):9586–9590; and Guevara-Garcia et al. (1993) *Plant J.* 4(3):495–505.

While it may be preferable to express the sequences using heterologous promoters, the native promoter sequences may be used. Such constructs would change expression levels of R protein in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126–6130); potyvirus leaders, for example, TEV leader (Tobacco Etch Virus) (Gallie et al. (1995) *Gene* 165(2):233–238), MDMV leader (Maize Dwarf Mosaic Virus) (*Virology* 154:9–20), and human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480483; Gossen (1993) Ph.D. Thesis, University of Heidelberg; Reines et al. (1993) *Proc. Natl. Acad. Sci. USA*

90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334:721–724. Such disclosures are herein incorporated by reference.

The above list of selectable marker genes is not meant to be limiting. Any selectable marker gene can be used in the present invention.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The sequences of the present invention can be used to transform or transfect any plant. In this manner, genetically modified plants, plant cells, plant tissue, seed, and the like can be obtained. Transformation protocols as well as protocols for introducing nucleotide sequences into plans may vary depending on the type of plant or plant cell, i.e. monocot or dicot, targeted for transformation. It is recognized that the transformation protocols may be used for transfection or introduction of the oligonucleotide sequences to disrupt R gene function. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad Sci. USA* 83:5602–5606, Agrobacterium-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature (London)* 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The present invention may be used for transformation of any plant species, including, but not limited to, monocots and dicots. Examples of plant species of interest include, but are not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus Cucumis such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The methods of the invention can be used with other methods for increasing pathogen resistance in plants. See, for example, Cai et al. (1997) *Science* 275:832–834; Roberts and Gallum (1984) *J. Heredity* 75:147–148; Ryerson and Heath (1996) *Plant Cell* 8:393–402 and Dangl et al. (1996) *Plant Cell* 8:1793–1807.

The R sequences of the invention are also useful as molecular markers. Such markers are useful in breeding programs, particularly those aimed at improving disease resistance. The sunflower R sequences have been mapped to chromosome locations and these positions related to known disease resistance loci.

The present invention provides a method of genotyping a plant comprising a polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson (1996) (Chapter 2) in: Genome Mapping in Plants (ed. Andrew H. Paterson) by Academic Press/R. G. Landis Company, Austin, Tex., pp. 7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene.

In the present invention, the nucleic acid probes employed for molecular marker mapping of plant nuclear genomes selectively hybridize, under selective hybridization conditions, to a gene encoding a polynucleotide of the present invention. In one embodiment, the probes are selected from polynucleotides of the present invention. Typically, these probes are cDNA probes or PstI genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single-stranded conformation analysis (SSCP); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Exemplary polymorphic variants are provided in Table I, supra. Thus, the present invention further provides a method of genotyping comprising the steps of contacting, under stringent hybridization conditions, a sample suspected of comprising a polynucleotide of the present invention with a nucleic acid prober. Generally, the sample is a plant sample; preferably, a sample suspected of comprising a sunflower polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In one embodiment, the nucleic acid probe comprises a polynucleotide of the present invention.

The following examples are offered by way of illustration and not by way of limitation.

EXPERIMENTAL

EXAMPLE 1

Cloning of Sunflower Disease Resistant Genes

MATERIALS AND METHODS

Plant Material

Sunflower plants and maize plants were grown in the greenhouse. For PCR-based isolation of R gene homologs and pto-like protein kinase genes we used the sunflower line SMF 3. Sunflower pathogen, *Scierotinia sclerotiorum* was maintained on PDA plate at 20° C. in dark.

PCR Amplification of Sunflower R Gene and Pto Homologs

To isolate R gene homologs, two conserved regions (NBS-LRR) of amino acid identity in the N gene from tobacco, the PRS2 gene from Arabidopsis, and the L6 gene from flax were used to design degenerate oligonucleotide primers as reported previously (Leister et al. (1998) *Proct. Natl. Acad. Sci. USA* 95:370–375) with the modifications as indicated in Table 1. Degenerate primers were designed based on motifs conserved between pto, fen, and APK1 in order to clone sunflower pto homologs. Table 1 summarizes the degenerate primers used for cloning R homologs and pto-like genes.

PCRs were performed in a total volume of 25 ul in 10 mM Tris-HCL, pH 8.3; 1.5 mM MgCL2; 50 mM KCL; 0.1 mM dNTPs; 0.25 uM of each primer with 0.5 units of advantage cDNA polymerase mix (Clontech) or Pwo DNA ploymerase (Boehringer). Genomic DNA and/or cDNA library mixtures were used as template for PCR amplification.

TABLE 1

Degenerate primers for isolating the R genes.

(A). NBS-LRR type R gene (N, Rps2, and L6 genes (18)):

| | |
|---|---|
| Sense: 5' GGN GGN RTN GGN AAN ACN AC 3' SEQ ID NO: 15 | biocode # 26433; |
| Antisense #1: 5' AG NGY NAG NGG NAG NCC 3' SEQ ID NO: 16 | biocode # 26924; |
| Antisense #2: 5' AG NGY NAG NGG NAA NCC 3' SEQ ID NO: 17 | biocode # 26925; |
| Antisense #3: 5' AG NGY NAA NGG NAG NCC 3' SEQ ID NO: 18 | biocode # 26926; |
| Antisense #4: 5' AG NGY NAA NGG NAA NCC 3' SEQ ID NO: 19 | biocode # 26927; |
| Antisense #5: 5' AA NGY NAG NGG NAG NCC 3' SEQ ID NO: 20 | biocode # 26928; |
| Antisense #6: 5' AA NGY NAG NGG NAA NCC 3' SEQ ID NO: 21 | biocode # 26929; |
| Antisense #7: 5' AA NGY NAA NGG NAG NCC 3' SEQ ID NO: 22 | biocode # 26930; |
| Antisense #8: 5' AA NGY NAA NGG NAA NCC 3' SEQ ID NO: 23 | biocode # 26931; |

(B). Primers for pto and fen homologous (16).

GFGDVYK:

| | |
|---|---|
| pto sense 1: 5' GGN TTY GGN RAN GTN TAY AA 3' SEQ ID NO: 24 | biocode # 26967; |
| pto sense 2: 5' GGN TTY GGN RAN GTN TAY AG 3' SEQ ID NO: 25 | biocode # 26968; |

GAA(R/K)GL:

| | |
|---|---|
| anti-sense: 5' TRN CCN YKN GCN GCN CC 3' SEQ ID NO: 26 | biocode # 26970; |

GFSYVD:

| | |
|---|---|
| anti-sense: 5' CCR AAN SYR TAN ACR TC 3' SEQ ID NO: 27 | biocode # 26971; |

\*\*R = A/G; Y = C/T; D = A/G/T; H = A/C/T; and N = A/G/T/C

Analysis of Amplified PCR Products

Amplified PCR fragments with the expected sizes of 450–550 bp for NBS-LRR primers, 340 bp for NBS primers and 600 bp for pto primers were individually sliced out of gels for a second round of PCR amplification with the same conditions as the initial PCR. Each second-round PCR amplification yielded a single band of the expected size which represented a heterogeneous population of PCR products. The PCR products were cloned into a TA vector (Clontech) according to the suppliers instructions. Fifty clones of each PCR product population were picked randomly and grouped by restriction analysis using 4-bp recognition enzymes (Alu I and Msp I). At least one representative clone of each identified group was selected for DNA sequencing using an Applied Biosystems 373A (ABI) automated sequencer at the Nucleic Acid Analysis Facility of Pioneer Hi-Bred International, Incorporated. DNA sequence analysis was carried out with the Sequencer (3.0). Multiple-sequence alignment (Clustal W) of the DNA sequence and phylogenetic analysis (PHYLIP) were made with the Curatool (CuraGen).

Construction of the Sclerotinia-infected and Resistance-enhanced (oxox-induced) Sunflower cDNA Libraries Six-week-old SMF3 sunflower plants were infected with *Sclerotinia sclerotritim* by petiole inoculation with Sclerotinia-infested carrot plugs. Six days after infection, leaf and stem tissues were collected from infected plants for total RNA isolation. Total RNA was also isolated from sunflower transgenic plants (SID 610255) expressing a wheat oxalate oxidase gene (oxox) at the six-week stage. Our previous studies have showed that elevated levels of $H_2O_2$, SA and PR1 protein were detected in oxox-transgenic plants at the six-week stage and the plants showed more resistance to Sclerotinia infection WO99/04013. mRNA was isolated using an mRNA purification kit (BRL) according to the manufacturer's instructions. cDNA libraries were constructed with the ZAP-cDNA synthesis kit into pBluescript phagemid (Stratagene). A cDNA library mixture for PCR cloning was made of oxox transgenic stem and Sclerotinia-infected leaf libraries (1:2 mix).

Isolation of Full-length or Flanking Sequences by PCR Amplification of cDNA Ends Full-length or flanking sequences of identified sunflower R gene and PK gene homologues were isolated using directly amplified Sclerotinia-infected cDNA libraries or the Marathon cDNA Amplification Kit (Clontech) according to the manufacturer's instructions. To facilitate cloning full-length cDNAs from the initial cloned regions, we designed a pair of 28 bp vector primers flanking the cloned cDNAs on both the 3' and 5' ends of the pBS vector. The vector primers were utilized to directionally amplify either a 5' or 3' end of a cDNA using one vector primer (pBS-upper or pBS-lower) and a gene-specific primer. Once the anticipated 5' end of a specific gene with an intact ATG start codon was cloned and sequenced, the full-length cDNA was amplified using a second gene-specific primer containing sequence upstream of the ATG and a vector primer at the 3' end. The PCR products were cloned and sequenced as described above.

RESULTS

Clone Full-length of cDNAs Related to Disease Resistance

A PCR-based cloning method to efficiently isolate full-length cDNAs of disease resistance-related R genes and protein kinase genes, as well as other plant defense genes, from sunflower cDNA libraries has been developed. A cDNA library mixture containing both oxox-transgenic cDNA library and Sclerotinia-infected cDNA library (1:2 mix) was used as a source of templates for PCR amplification. Using cDNA libraries as a source of DNA templates for PCR amplification had two benefits: (1) the number of unexpected PCR products was reduced as compared with genomic DNA as a source of templates and (2) disease-induced cDNA libraries increased the chance of isolating defense-related genes. To facilitate cloning full-length cDNAs from the initially cloned regions, a pair of 28 bp vector primers (Table 2) the flanking cDNAs on the ends (3' and 5') of pBS vector was designed and used to directionally amplify either the 5' or 3' end of the cDNA with one of the vector primers paired with a gene-specific primer (Table 2a and 2b). The 5' end of the gene with the intact ATG start codon was cloned and sequenced. The full-length cDNA was amplified by using a second gene-specific primer containing the upstream ATG region sequence and a vector primer at the 3' end. The PCR products were cloned and sequenced as described above. This method was used in the full-length clone isolation as indicated below.

TABLE 2

Gene Specific primers for R end RACE and full length cloning (A): Specific primers for R gene end RACE

| | |
|---|---|
| RS-1: CGATGTGAAGGTAGGGAATGAG SEQ ID NO: 28 | Biocode: 27101; |
| RS-2: GGGAGTGAGATAATAGGAAGGAGC SEQ ID NO: 29 | Biocode: 27102; |
| RS-3: GGTAGGGAGTGAGATAGAAGGAAG SEQ ID NO: 30 | Biocode: 27103; |
| RS-4: TATGAAGTGAATTTGTTATCACA SEQ ID NO: 31 | Biocode: 27104; |
| RS-5: TATGAAGTGAGTTTGTTATCACA SEQ ID NO: 32 | Biocode: 27105; |
| RS-6: AAGACGACTCTCGCATCTGCTGCCTA SEQ ID NO: 33 | Biocode: 27166; |
| RS-7: GAAGACGACTCTCGCATCTGCTGCTT SEQ ID NO: 34 | Biocode: 27167; |
| RAS-1: GCCACCAGCATAAGAAACTACC SEQ ID NO: 35 | Biocode: 27106; |
| RAS-2: GGCCGTCAGCATAAGAAACTAC SEQ ID NO: 36 | Biocode: 27107; |
| RAS-3: GGAGGCCACTAGCATAAGAAAC SEQ ID NO: 37 | Biocode: 27108; |
| RAS-4: GGGGAGGCCACCAGCATAAGAAACTA SEQ ID NO: 38 | Biocode: 27168; |
| RAS-5: CGAAGGGGAGGCCACTAGCATAAGAA SEQ ID NO: 39 | Biocode: 27169; |
| RAS-6: CAATTATTATCCGGCTCCCCTCACCA SEQ ID NO: 40 | Biocode: 27170; |
| RAS-7: TCTTATATCGTGTCTGCATGGCGGGT SEQ ID NO: 41 | Biocode: 27171; |
| RAS-8: CACTTCATAAATCGTTTGCGCCCTGC SEQ ID NO: 42 | Biocode: 27172; |

(B) PK SPECIFIC PRIMERS FOR RACE:

| | |
|---|---|
| PKS1 *: GCAGCGGTCAGATTGTAGCTGTCAAA SEQ ID NO: 43 Group 1 | biocode: 27884; |
| PKAS1: GCCAGCCGCTATCTTCATTCTTGTGT SEQ ID NO: 44 | biocode: 27885; |
| PKS2: GGATAGGAACGGGCTGCAGGGTAAC SEQ ID NO: 45 | biocode: 27886; |
| PKAS2: TTTGGTCACCATCAGCACAGTATCCG SEQ ID NO: 46 | biocode: 27887; |
| PKS3: CTTGGGTTTGGGGAGGTGTACAGAGG SEQ ID NO: 47 | biocode: 27888; |
| PKS4: CTTGGATGCTGCAATTAAGCGACTGG SEQ ID NO: 48 Group 2 | biocode: 27889; |
| PKAS4: GGCGGCGCCTATGCATATTTTGAGT SEQ ID NO: 49 | biocode: 27890; |
| PKS5: CTTCAAAACCGGGGTCTGGAGTCGTT SEQ ID NO: 50 Group 3 | biocode: 27891; |
| PKAS5: CGGAGACTCCATGTTAGCGGTTGAAA SEQ ID NO: 51 | biocode: 27892; |

(C) PK primers for full length cloning:

| | |
|---|---|
| PK4-RACE: AACTATGTCTTTCCATACCAGTCACCCGG SEQ ID NO: 52 | biocode: 29131; |
| PK5-RACE: TCGGAGACTCCATGTTAGCGGTTAA SEQ ID NO: 53 | biocode: 29132; |
| PK1-RACE: GACCGTTCCTTCAATTAATGGGTTGC SEQ ID NO: 54 | biocode: 29136; |

TABLE 2-continued

Gene Specific primers for R end RACE and full length cloning

Vector primers

| | |
|---|---|
| PBS-upper: GCGATTAAGTTGGGTAACGCCAGGGT SEQ ID NO: 55 | biocode: 27164; |
| PBS-lower: TCCGGCTCGTATGTTGTGTGGAATTG SEQ ID NO: 56 | biocode: 27165; |

*: RS primers: for cloning 3' end of cDNA clones and RAS for cloning 5' end of cDNAs.
*PKS for the 3' end ofcDNA clones and PKAS for the 5' end clones
**Group 1 (PK1): clones pto-1,-8,-16,-18
Group 2 (PK4): clone pto-21
Group 3 (PK5): clone pto-6

Protein Kinase cDNAs

Four different full-length PK cDNAs have been cloned from sunflower cDNA libraries. Isolation of full-length PK cDNA clones was performed with three rounds of cloning efforts using PCR-based techniques. The first step of the PK cloning was performed by PCR amplification using degenerate primers based on conserved regions between pto, fen and an Arabidopsis PK (Table 1). The initial PCR amplification resulted in the expected bands (about 350 bp). The anticipated PCR products were isolated from the gel, and then re-amplified. The PCR products were cloned into TA vectors. Restriction digestions of cloned fragments with Alu I and Msp I resulted in several different patterns. Six clones were identified as PK positive. Four of the six PK clones showed differences only at the degenerate primer regions and were considered as one group. PK positive clones were classified into three different groups of PK homologous (PK1, PK4 and PK5) based on sequence similarity. Gene-specific primers (Table 2b) were made for cloning of the 3' and 5' end of the three different groups of PK. Finally, PK clones containing 5' end sequence were used to design new primers (Table 2c) for cloning full-length cDNA clones. The amino acid sequence of PK1A is highly similar to that of PK1B (FIG. 1). Both are closely related to PTO kinase from tomato (FIG. 1), which is a disease resistance protein against bacterial speck disease. Sequence comparison indicated that PK4 was highly similar to a receptor-like protein kinase and disease resistance protein kinase. Currently, for the PK5 group, only one 5'-end clone has been sequenced. It had 971 bp long and coded a 170 amino acid protein. A BLASTX search showed it had 68% identity with protein kinase APK1A from Arabidopsis.

NBS-LRR Type R Gene Homologs

The PCR products were amplified from sunflower and maize genomic DNAs and sunflower cDNA libraries using degenerate primers. One major expected band of about 500 bp was amplified from a sunflower source using NBS-LRR primers. A similar size band was amplified from maize genomic DNA. These expected bands amplified from the cDNA library mix were isolated and/or re-amplified, and then cloned into TA vectors. Separate PCR amplifications of sunflower genomic DNA and cDNAs using degenerate NBS-LRR primers each produced a large band around 500 bp. Restriction digestion of cloned fragments with Alu I and Msp I resulted in several different patterns. The presence of a heterogeneous PCR product suggested the involvement of a multigene family. At least one representative clone was selected from each different digestion group for sequence analysis. A total of six different R gene homologs from sunflower were identified using the BLAST algorithm to search GenBank. Based on the initial sequence information several gene specific primers were made (Table 1b) to clone both the 5' and 3' ends by PCR amplification. Four clones have been isolated. Two 3'-end clones (RS6-8 and RS7-4) and two 5'-end clones (RAS4-5 and RAS5-1) can form two contigs (RS6-8 contig and RS7-4 contig) (SEQ ID NOs: 7, 9–12, and 14). Both contigs showed high homology with the tobacco mosaic virus (TMV) resistance gene N, the downy mildew resistance gene and the rust resistance gene (FIGS. 3 and 4). In summary, six NBS-LRR type homologs were isolated using a PCR-based cloning strategy. R homolog clones from sunflower showed the highest homology to the R genes from other dicot plants

EXAMPLE 2

Transformation and Regeneration of Transgenic Maize Plants

Immature maize embryos from greenhouse donor plants are bombarded with a plasmid containing the R gene operably linked to a UBI promoter (FIG. 5) and the selectable marker gene PAT (Wohlleben et al. (1988) Gene 70:25–37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the R gene operably linked to a UBI promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for disease resistance.

Bombardment and Culture Media

Bombardment medium (560Y) comprises 4.0 g/l N6 basal salts (SIGMA C-1416), 1.0 ml/l Eriksson's Vitamin Mix (1000X SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000X SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) Physiol. Plant. 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-1 $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

EXAMPLE 3

Virus-mediated Transformation

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

The nucleotide constructs of the invention may be introduced into plants by contacting plants with a virus or viral nucleic acids. Generally, such methods involve incorporating a nucleotide construct of the invention within a viral DNA or RNA molecule. It is recognized that the an R protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

EXAMPLE 4

Agrobacterium-mediated Transformation

For Agrobacterium-mediated transformation of maize with an R gene, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of Agrobacterium, where the bacteria are capable of transferring the R gene to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

EXAMPLE 5

Transformation and Regeneration of Transgenic Soybean Embryos

Soybean embryos are bombarded with a plasmid containing the R gene operably linked to a UBI promoter (FIG. 5) as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) Nature (London) 327:70–73, U.S. Pat. No. 4,945,050). A Du Pont Biolistic PDS 1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) Nature 313:810–812), the hygromycin phosphotransferase gene from plasmid pJR225 (from *E. coli*; Gritz et al. (1983) Gene 25:179–188), and the 3' region of the nopaline synthase gene from the T-DNA of the Ti plasmid of *Agrobacterium tumefaciens*. The expression cassette comprising the R gene operably linked to the UBI promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 6

Transformation and Regeneration of Sunflower Meristem Tissues

Sunflower meristem tissues are transformed with an expression cassette containing the R gene operably linked to a UBI promoter as follows (see also European Patent Number EP 0 486233, herein incorporated by reference, and Malone-Schoneberg et al. (1994) *Plant Science* 103:199–207). Mature sunflower seed (*Helianthus annuus* L.) are dehulled using a single wheat-head thresher. Seeds are surface sterilized for 30 minutes in a 20% Chlorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al. (1990) *Plant Cell Rep.* 9: 55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15: 473–497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to Agrobacterium treatment (Bidney et al. (1992) *Plant Mol. Biol.* 18: 301–313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the R gene operably linked to the UBI promoter is introduced into Agrobacterium strain EHA105 via freeze-thawing as described by Holsters et al. (1978) *Mol. Gen. Genet.* 163:181–187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The Agrobacterium cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an Agrobacterium suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for R protein activity.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by the R protein activity analysis of leaf extracts while transgenic seeds harvested from NPTII-positive $T_0$ plants are identified by the R protein activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Chlorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 $\mu$m tungsten particles are resuspended in 150 $\mu$l absolute ethanol. After sonication, 8 $\mu$l of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28 ° C. in a liquid YEP medium (10 g/l yeast extract, 10 g/l Bactopeptone, and 5 g/l NaCl, pH 7.0) in the presence of 50 $\mu$g/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 $\mu$g/ml cefotaxime). The plantlets are cultured on the medium for about two weeks under 16-hour day and 26° C. incubation conditions.

Explants (around 2 cm long) from two weeks of culture in 374C medium are screened for R protein activity using assays known in the art. After positive (i.e., for R protein expression) explants are identified, those shoots that fail to exhibit R protein activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for R protein expression are grafted to Pioneer hybrid 6440 in vitro-grown sunflower seedling rootstock. The rootstocks are prepared in the following manner. Seeds are dehulled and surface-sterilized for 20 minutes in a 20% Chlorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for creating or enhancing disease resistance in a plant, said method comprising:

(a) introducing into a plant cell a recombinant expression cassette comprising a sunflower R nucleotide sequence operably linked to a promoter that drives expression in a plant, wherein said R nucleotide sequence is selected from the group consisting of:

(i) a nucleotide sequence encoding the amino acid sequence set forth in SEQ ID NO: 2; and (ii) the nucleotide sequence set forth in SEQ ID NO: 1;

(b) culturing the plant cell under plant cell growing conditions; and (c) regenerating from the plant cell a whole plant, wherein the plant has enhanced or newly created disease resistance.

2. The method of claim 1, wherein said plant is a monocot.

3. The method of claim 2, wherein said monocot is maize, rice, or wheat.

4. The method of claim 1, wherein said plant is a dicot.

5. The method of claim 4, wherein said dicot is sunflower, soybean, canola or alfalfa.

6. A plant having stably incorporated in its genome a DNA construct, said construct comprising a promoter that drives expression in a plant operably linked to a sunflower R nucleotide sequence, wherein said R nucleotide sequence is selected from the group consisting of:

(a) a nucleotide sequence encoding the amino acid sequence set forth in SEQ ID NO: 2; and (b) the nucleotide sequence set forth in SEQ ID NO: 1.

7. The plant of claim 6, wherein said plant is a monocot.

8. The plant of claim 7, wherein said monocot is maize, rice or wheat.

9. The plant of claim 6, wherein said plant is a dicot.

10. The plant of claim 9, wherein said dicot is sunflower, soybean, canola or alfalfa.

11. Transformed seed of the plant of any one of claims 6–10 inclusive, wherein the seed comprise the construct.

12. A plant cell having stably incorporated in its genome a DNA construct, said construct comprising a promoter that drives expression in a plant cell operably linked to a sunflower R nucleotide sequence, wherein said R nucleotide sequence is selected from the group consisting of:

(a) a nucleotide sequence encoding the amino acid sequence set forth in SEQ ID NO: 2; and (b) the nucleotide sequence set forth in SEQ ID NO: 1.

13. The plant cell of claim 12, wherein said plant cell is from a monocot.

14. The plant cell of claim 12, wherein said plant cell is from a dicot.

15. An isolated nucleotide sequence said sequence comprising at least one of the nucleotide sequences selected from the group consisting of:

(a) a nucleotide sequence encoding the amino acid sequence set forth in SEQ ID NO: 2; and (b) the nucleotide sequence set forth in SEQ ID NO: 1.

16. A chimeric gene comprising a promoter operably linked to the nucleotide sequence of claim 15.

17. A vector comprising the chimeric gene of claim 16.

18. A plant cell transformed with the vector of claim 17.

19. A plant regenerated from the plant cell of claim 18.

20. A method for modulating cellular metabolism in a plant, said method comprising (a) introducing into a plant cell a recombinant expression cassette comprising a promoter that drives expression in a plant cell operably linked to a nucleic acid sequence selected from the group consisting of;
  (i) a nucleotide sequence encoding the amino acid sequence set forth in SEQ ID NO: 2; and
  (ii) the nucleotide sequence set forth in SEQ ID NO: 1;
(b) culturing the plant cell under plant cell growing conditions; and
(c) regenerating from the plant cell a whole plant, wherein the plant has modulated cellular metabolism.

21. A method for creating or enhancing disease resistance in a plant, said method comprising:
  (a) introducing into a plant cell a recombinant expression cassette comprising a sunflower R nucleotide sequence operably linked to a promoter that drives expression in a plant, wherein said R nucleotide sequence comprises a nucleotide sequence that has at least about 95% sequence identity to the sequence set forth in SEQ ID NO: 1, wherein said nucleotide sequence encodes an R protein;
  (b) culturing the plant cell under plant cell growing conditions; and
  (c) regenerating from the plant cell a whole plant, wherein the plant has enhanced or newly created disease resistance.

22. The method of claim 21, wherein said plant is a monocot.

23. The method of claim 22, wherein said monocot is maize, rice, or wheat.

24. The method of claim 21, wherein said plant is a dicot.

25. The method of claim 24, wherein said dicot is sunflower, soybean, canola or alfalfa.

26. A plant having stably incorporated in its genome a DNA construct, said construct comprising a promoter that drives expression in a plant operably linked to a sunflower R nucleotide sequence, wherein said R nucleotide sequence comprises a nucleotide sequence that has at least about 95% sequence identity to the sequence set forth in SEQ ID NO:1, wherein said nucleotide sequence encodes an R protein.

27. The plant of claim 26, wherein said plant is a monocot.

28. The plant of claim 27, wherein said monocot is maize, rice or wheat.

29. The plant of claim 26, wherein said plant is a dicot.

30. The plant of claim 29, wherein said dicot is sunflower, soybean, canola or alfalfa.

31. Transformed seed of the plant of any one of claims 26–30 inclusive, wherein the seed comprise the construct.

32. A plant cell having stably incorporated in its genome a DNA construct, said construct comprising a promoter that drives expression in a plant cell operably linked to a sunflower R nucleotide sequence, wherein said R nucleotide sequence comprises a nucleotide sequence that has at least about 95% sequence identity to the sequence set forth in SEQ ID NO:1, wherein said nucleotide sequence encodes an R protein.

33. The plant cell of claim 32, wherein said plant cell is from a monocot.

34. The plant cell of claim 32, wherein said plant cell is from a dicot.

35. An isolated nucleotide sequence, said sequence comprising a nucleotide sequence that has at least about 95% sequence identity to the sequence set forth in SEQ ID NO:1, wherein said nucleotide sequence encodes an R protein.

36. A chimeric gene comprising a promoter operably linked to the nucleotide sequence of claim 35.

37. A vector comprising the chimeric gene of claim 36.

38. A plant cell transformed with the vector of claim 37.

39. A plant regenerated from the plant cell of claim 38.

40. A method for modulating cellular metabolism in a plant, said method comprising
  (a) introducing into a plant cell a recombinant expression cassette comprising a promoter that drives expression in a plant cell operably linked to a sunflower R nucleotide sequence, wherein said R nucleotide sequence comprises a nucleotide sequence that has at least about 95% sequence identity to the sequence set forth in SEQ ID NO:1, wherein said nucleotide sequence encodes an R protein;
  (b) culturing the plant cell under plant cell growing conditions; and
  (c) regenerating from the plant cell a whole plant, wherein the plant has modulated cellular metabolism.

* * * * *

SEQUENCE LISTING

```
<160> NUMBER OF SEQ ID NOS: 64

<210> SEQ ID NO 1
<211> LENGTH: 1593
<212> TYPE: DNA
<213> ORGANISM: Helianthus annuus
<220> FEATURE:

<400> SEQUENCE: 1
ttccttcaat ta atg ggt tgc ttt tct tgt ttc gat tca aag gaa gat gga        51 aaa tct aag cct caa aag act agg gct gat cac aat gaa gtt cac cca          99 tct gcc cct tca aat atc tca aga tta cct tct ggt ttg gat aga cag         147 aaa tct aga aat aat gtt agt ttg agg aaa gaa tcg tcg ggt tcg aaa         195 gac ggg tcg cag ggt cag att gct gct cat aca ttc act ttc cgg gag         243 ctt gca gct gca aca aac aat ttt agc cct gat tgt ttg cta gga gaa         291 gga ggg ttt ggc cat gtg tat aga gga cgg ctt ccg ggc agc ggt cag         339 att gta gct gtc aaa caa ttg gat agg aac ggg ctg cag ggt aac cgt         387 gaa ttt ctc gta gaa gtt ctt atg ctc agc ctt tta cat cat ccc aat         435 ttg gtg aat tta atc gga tac tgt gct gat ggt gac caa aga ctt ctt         483 gtt tat gaa ttc atg cca ttg gga tcg tta gaa gat cat ctt cat gat         531 ctc cca cca gaa aaa gaa gcg tta gat tgg aac aca aga atg aag ata         579 gcg gct ggt gca gct cga ggt ttg gaa ttt ctt cac gat aag gct aat         627 cct cct gtt att tac agg gat ttc aaa tca tca aac att ttg ctc ggt         675 gag gga ttt caa cca aag ctt tct gat ttc ggg cta gcg aag ttg ggc         723 ccg acg gga gat aag tct cat gta tcc aca cgg gtc atg gga acg tat         771 ggt tac tgt gct cct gag tat gcg atg acc ggt caa ctc act gtt aag         819 tct gat gtg tat agc ttt ggg gtg gtt ttc tta gag ctt att aca ggc         867 cga aaa gcc att gac agc agt gca ccg caa gga cag cag aat ctc gtc         915
```

```
act tgg gca cga ccc tta ttc aac gac aga agg aaa ttt gca aca ttg      963 gca gac ccc agg ctt gaa gga cat tat ccc atg agg ggt ctg tac cag     1011 gct cta gcg gtt gca tcg atg tgc atc caa gaa cag gct gcg gct cga     1059 ccg ctt ata gga gac gtg gtc act gcc tta tct tat ctt gcg aac cac     1107 acc tat gat ccc aat gcg gcc tct ggt caa agc aac cgg tac aac aac     1155 ggt gag aga acc agt aga att tca aag aat gaa gaa ggt ggt ggg tcg     1203 ggt cgt agc agg tgg ggg gat cta gaa ggt tcc gac aaa gga gat tcg     1251 cct cga gaa act caa act cca agg atg ctg aat cga gat ctt gat cga     1299 gaa cgg gct gtt gct gag gct aaa atg tgg gta gaa aaa aga cga caa     1347 agt gca caa ggc agc ttt gat ggg aat gct aac ggt taagagacga          1393 gtgttggtgc gttactgtgg tgttttgaac ttttgaccac cacgatttga ttttttttctt  1453 ttgttttccc tgtacccgat tcaggagaaa aaattcggat aaacaggcgg gtgtttatgt   1513
ataccaaata tgaggtgaat gggaaaactt attatggttt atgggttatt ttgttgttgt   1573
aaaaaaaaaa aaaaaaaaa                                                 1593
```

<210> SEQ ID NO 2
<211> LENGTH: 457
<212> TYPE: PRT
<213> ORGANISM: Helianthus annuus

<400> SEQUENCE: 2

```
Met Gly Cys Phe Ser Cys Phe Asp Ser Lys Glu Asp Gly Lys Ser Lys
 1               5                  10                  15

Pro Gln Lys Thr Arg Ala Asp His Asn Glu Val His Pro Ser Ala Pro
             20                  25                  30

Ser Asn Ile Ser Arg Leu Pro Ser Gly Leu Asp Arg Gln Lys Ser Arg
         35                  40                  45

Asn Asn Val Ser Leu Arg Lys Glu Ser Ser Gly Ser Lys Asp Gly Ser
     50                  55                  60

Gln Gly Gln Ile Ala Ala His Thr Phe Thr Phe Arg Glu Leu Ala Ala
 65                  70                  75                  80

Ala Thr Asn Asn Phe Ser Pro Asp Cys Leu Leu Gly Glu Gly Gly Phe
                 85                  90                  95

Gly His Val Tyr Arg Gly Arg Leu Pro Gly Ser Gly Gln Ile Val Ala
            100                 105                 110

Val Lys Gln Leu Asp Arg Asn Gly Leu Gln Gly Asn Arg Glu Phe Leu
        115                 120                 125

Val Glu Val Leu Met Leu Ser Leu His His Pro Asn Leu Val Asn
    130                 135                 140

Leu Ile Gly Tyr Cys Ala Asp Gly Asp Gln Arg Leu Leu Val Tyr Glu
145                 150                 155                 160

Phe Met Pro Leu Gly Ser Leu Glu Asp His Leu His Asp Leu Pro Pro
                165                 170                 175

Glu Lys Glu Ala Leu Asp Trp Asn Thr Arg Met Lys Ile Ala Ala Gly
            180                 185                 190

Ala Ala Arg Gly Leu Glu Phe Leu His Asp Lys Ala Asn Pro Pro Val
        195                 200                 205

Ile Tyr Arg Asp Phe Lys Ser Ser Asn Ile Leu Leu Gly Glu Gly Phe
    210                 215                 220
```

```
Gln Pro Lys Leu Ser Asp Phe Gly Leu Ala Lys Leu Gly Pro Thr Gly
225                 230                 235                 240

Asp Lys Ser His Val Ser Thr Arg Val Met Gly Thr Tyr Gly Tyr Cys
            245                 250                 255

Ala Pro Glu Tyr Ala Met Thr Gly Gln Leu Thr Val Lys Ser Asp Val
            260                 265                 270

Tyr Ser Phe Gly Val Val Phe Leu Glu Leu Ile Thr Gly Arg Lys Ala
        275                 280                 285

Ile Asp Ser Ser Ala Pro Gln Gly Gln Gln Asn Leu Val Thr Trp Ala
290                 295                 300

Arg Pro Leu Phe Asn Asp Arg Arg Lys Phe Ala Thr Leu Ala Asp Pro
305                 310                 315                 320

Arg Leu Glu Gly His Tyr Pro Met Arg Gly Leu Tyr Gln Ala Leu Ala
                325                 330                 335

Val Ala Ser Met Cys Ile Gln Glu Gln Ala Ala Arg Pro Leu Ile
            340                 345                 350

Gly Asp Val Val Thr Ala Leu Ser Tyr Leu Ala Asn His Thr Tyr Asp
        355                 360                 365

Pro Asn Ala Ala Ser Gly Gln Ser Asn Arg Tyr Asn Asn Gly Glu Arg
    370                 375                 380

Thr Ser Arg Ile Ser Lys Asn Glu Glu Gly Gly Ser Gly Arg Ser
385                 390                 395                 400

Arg Trp Gly Asp Leu Glu Gly Ser Asp Lys Gly Asp Ser Pro Arg Glu
                405                 410                 415

Thr Gln Thr Pro Arg Met Leu Asn Arg Asp Leu Asp Arg Glu Arg Ala
            420                 425                 430

Val Ala Glu Ala Lys Met Trp Val Glu Lys Arg Arg Gln Ser Ala Gln
        435                 440                 445

Gly Ser Phe Asp Gly Asn Ala Asn Gly
    450                 455

<210> SEQ ID NO 3
<211> LENGTH: 1559
<212> TYPE: DNA
<213> ORGANISM: Helianthus annuus
<220> FEATURE:
<221> NAME/KEY: CDS
<222> LOCATION: (81)...(1319)

<400> SEQUENCE: 3
tcggcttcgt taccttacct tcttcatcgt cggcatcatt tatccatatc caacttaacg    60
gtttcatcta gattacagta atg ggt tgt ttt cct tgc ttt gaa tcc agt caa   113
                     Met Gly Cys Phe Pro Cys Phe Glu Ser Ser Gln
                      1               5                  10 gag gac aac aac ttc aat cac caa aaa gtc ggc cat gaa gtc cac cca   161
Glu Asp Asn Asn Phe Asn His Gln Lys Val Gly His Glu Val His Pro
            15                  20                  25 tcc gcc cct tcc aat att tcc aga tta tct tcc ggg gtt gat agg atg   209
Ser Ala Pro Ser Asn Ile Ser Arg Leu Ser Ser Gly Val Asp Arg Met
        30                  35                  40 aaa acg aga aac aat gtt aat aat gct gct agc cta agg agg gag tca   257
Lys Thr Arg Asn Asn Val Asn Asn Ala Ala Ser Leu Arg Arg Glu Ser
    45                  50                  55 tca ggg ccg ccg gat gct caa atc gcc gca caa acc ttc aca ttc cgc   305
Ser Gly Pro Pro Asp Ala Gln Ile Ala Ala Gln Thr Phe Thr Phe Arg
60                  65                  70                  75 gag ctt gca gcc gcc acc aat aat ttt cag cct gat tgc ttc tta agg   353
```

```
                                                                  -continued Glu Leu Ala Ala Ala Thr Asn Asn Phe Gln Pro Asp Cys Phe Leu Arg
                80                  85                  90 gag ggt ggt ttt ggt tgt gta tat aga gga cgt ctt cag agt agt ggt        401
Glu Gly Gly Phe Gly Cys Val Tyr Arg Gly Arg Leu Gln Ser Ser Gly
                95                 100                 105 caa gtt gta gct gtt aaa cag ctg gat aga aat gga ctc caa ggt aac        449
Gln Val Val Ala Val Lys Gln Leu Asp Arg Asn Gly Leu Gln Gly Asn
            110                 115                 120 cgt gag ttt ctt gtt gaa gtt ctt atg ctc agc ctt tta cat cat cca        497
Arg Glu Phe Leu Val Glu Val Leu Met Leu Ser Leu Leu His His Pro
        125                 130                 135 aac ttg gtc aat ttg att ggc tac tgc gct gac ggt gac caa cga ctt        545
Asn Leu Val Asn Leu Ile Gly Tyr Cys Ala Asp Gly Asp Gln Arg Leu
140                 145                 150                 155 ctt gtc tat gag ttt atg gcc ttg ggt tcc ttg gaa gat cac ctt cat        593
Leu Val Tyr Glu Phe Met Ala Leu Gly Ser Leu Glu Asp His Leu His
                160                 165                 170 gat gtt ccg cct gac aga gaa cca tta gat tgg aca cag gat gaa gat        641
Asp Val Pro Pro Asp Arg Glu Pro Leu Asp Trp Thr Gln Asp Glu Asp
            175                 180                 185 agc ggc tgt gca gcc aag ggg ttg gag ttt ctt cat gat aaa gct aac        689
Ser Gly Cys Ala Ala Lys Gly Leu Glu Phe Leu His Asp Lys Ala Asn
        190                 195                 200 cca cca gtt att tat cgg gac ttc aaa tca tca aac att ttg ctg gat        737
Pro Pro Val Ile Tyr Arg Asp Phe Lys Ser Ser Asn Ile Leu Leu Asp
    205                 210                 215 gag gga ttt caa cca aag ctg tcc gac ttc ggg ctc gcg aaa ctg ggc        785
Glu Gly Phe Gln Pro Lys Leu Ser Asp Phe Gly Leu Ala Lys Leu Gly
220                 225                 230                 235 ccc act gga gac aag tct cat gtt tcc aca cgg gtg atg ggt aca tac        833
Pro Thr Gly Asp Lys Ser His Val Ser Thr Arg Val Met Gly Thr Tyr
                240                 245                 250 ggt tac tgt gct cct gag tat gcc atg act ggt cag tta acg gtc aaa        881
Gly Tyr Cys Ala Pro Glu Tyr Ala Met Thr Gly Gln Leu Thr Val Lys
            255                 260                 265 tcc gat gtg tac agc ttt ggt gtc gtc ttt tta gag ctt att acc ggt        929
Ser Asp Val Tyr Ser Phe Gly Val Val Phe Leu Glu Leu Ile Thr Gly
        270                 275                 280 aga aaa gcc ata gat agc act caa cca cat gga cag cag aac ctg gtg        977
Arg Lys Ala Ile Asp Ser Thr Gln Pro His Gly Gln Gln Asn Leu Val
    285                 290                 295 aca tgg gca cga cct ttg ttc aac gac aga agg aaa ttc aca tcg ttg       1025
Thr Trp Ala Arg Pro Leu Phe Asn Asp Arg Arg Lys Phe Thr Ser Leu
300                 305                 310                 315 gtg gac cca cgg tta gaa ggt cgg tac cca atg cgg ggg ctg tac cag       1073
Val Asp Pro Arg Leu Glu Gly Arg Tyr Pro Met Arg Gly Leu Tyr Gln
                320                 325                 330 gcg cta gcg gtg gca tcc atg tgt att caa gaa cag gtt gca gcc cgg       1121
Ala Leu Ala Val Ala Ser Met Cys Ile Gln Glu Gln Val Ala Ala Arg
            335                 340                 345 cct ttg att gct gac gtg gta act gcg cta tct tat ctt gca aac cag       1169
Pro Leu Ile Ala Asp Val Val Thr Ala Leu Ser Tyr Leu Ala Asn Gln
        350                 355                 360 ggg tac gat ccg acc aca gct ccc agc ttc ata aca tca tca gca gcg       1217
Gly Tyr Asp Pro Thr Thr Ala Pro Ser Phe Ile Thr Ser Ser Ala Ala
    365                 370                 375 ccg gcg gca agg aga gac tta aaa ccg caa ggt ttt cga aaa acg atg       1265
Pro Ala Ala Arg Arg Asp Leu Lys Pro Gln Gly Phe Arg Lys Thr Met
380                 385                 390                 395
```

```
aag ggg gtt gca gca gat ggg att tgg aag aat cgg att ctc cca aag    1313
Lys Gly Val Ala Ala Asp Gly Ile Trp Lys Asn Arg Ile Leu Pro Lys
            400                 405                 410 aaa ctg taaagatgct tgagagagaa agggctgttg cagaagcaaa aatgtgggtt    1369
Lys Leu gaaaaaagaa gacagagtgg gtagtagatg tttgttttac atacattgtt cagatgatga    1429
ttcaaagggt gggttgttga caaagtccaa accaattttt ctgcagtaat attgtatgta    1489
tatttcttat gggaaaagag gagatcaaac agaacttaaa ggtcggcttg attgaaaaaa    1549
aaaaaaaaaa                                                           1559
```

<210> SEQ ID NO 4
<211> LENGTH: 413
<212> TYPE: PRT
<213> ORGANISM: Helianthus annuus

<400> SEQUENCE: 4

```
Met Gly Cys Phe Pro Cys Phe Glu Ser Ser Gln Glu Asp Asn Asn Phe
  1               5                  10                  15

Asn His Gln Lys Val Gly His Glu Val His Pro Ser Ala Pro Ser Asn
             20                  25                  30

Ile Ser Arg Leu Ser Ser Gly Val Asp Arg Met Lys Thr Arg Asn Asn
         35                  40                  45

Val Asn Asn Ala Ala Ser Leu Arg Arg Glu Ser Ser Gly Pro Pro Asp
 50                  55                  60

Ala Gln Ile Ala Ala Gln Thr Phe Thr Phe Arg Glu Leu Ala Ala Ala
 65                  70                  75                  80

Thr Asn Asn Phe Gln Pro Asp Cys Phe Leu Arg Glu Gly Gly Phe Gly
                 85                  90                  95

Cys Val Tyr Arg Gly Arg Leu Gln Ser Ser Gly Gln Val Val Ala Val
            100                 105                 110

Lys Gln Leu Asp Arg Asn Gly Leu Gln Gly Asn Arg Glu Phe Leu Val
        115                 120                 125

Glu Val Leu Met Leu Ser Leu His His Pro Asn Leu Val Asn Leu
130                 135                 140

Ile Gly Tyr Cys Ala Asp Gly Asp Gln Arg Leu Leu Val Tyr Glu Phe
145                 150                 155                 160

Met Ala Leu Gly Ser Leu Glu Asp His Leu His Asp Val Pro Pro Asp
                165                 170                 175

Arg Glu Pro Leu Asp Trp Thr Gln Asp Glu Asp Ser Gly Cys Ala Ala
            180                 185                 190

Lys Gly Leu Glu Phe Leu His Asp Lys Ala Asn Pro Val Ile Tyr
        195                 200                 205

Arg Asp Phe Lys Ser Ser Asn Ile Leu Leu Asp Glu Gly Phe Gln Pro
210                 215                 220

Lys Leu Ser Asp Phe Gly Leu Ala Lys Leu Gly Pro Thr Gly Asp Lys
225                 230                 235                 240

Ser His Val Ser Thr Arg Val Met Gly Thr Tyr Gly Tyr Cys Ala Pro
                245                 250                 255

Glu Tyr Ala Met Thr Gly Gln Leu Thr Val Lys Ser Asp Val Tyr Ser
            260                 265                 270

Phe Gly Val Val Phe Leu Glu Leu Ile Thr Gly Arg Lys Ala Ile Asp
        275                 280                 285

Ser Thr Gln Pro His Gly Gln Gln Asn Leu Val Thr Trp Ala Arg Pro
290                 295                 300
```

```
Leu Phe Asn Asp Arg Arg Lys Phe Thr Ser Leu Val Asp Pro Arg Leu
305                 310                 315                 320

Glu Gly Arg Tyr Pro Met Arg Gly Leu Tyr Gln Ala Leu Ala Val Ala
                325                 330                 335

Ser Met Cys Ile Gln Glu Gln Val Ala Ala Arg Pro Leu Ile Ala Asp
            340                 345                 350

Val Val Thr Ala Leu Ser Tyr Leu Ala Asn Gln Gly Tyr Asp Pro Thr
        355                 360                 365

Thr Ala Pro Ser Phe Ile Thr Ser Ser Ala Ala Pro Ala Ala Arg Arg
    370                 375                 380

Asp Leu Lys Pro Gln Gly Phe Arg Lys Thr Met Lys Gly Val Ala Ala
385                 390                 395                 400

Asp Gly Ile Trp Lys Asn Arg Ile Leu Pro Lys Lys Leu
                405                 410

<210> SEQ ID NO 5
<211> LENGTH: 2114
<212> TYPE: DNA
<213> ORGANISM: Helianthus annuus
<220> FEATURE:
<221> NAME/KEY: misc_feature
<222> LOCATION: (1)...(2114)
<223> OTHER INFORMATION: n = A,T,C or G
<220> FEATURE:
<221> NAME/KEY: misc_feature
<222> LOCATION: 1475
<223> OTHER INFORMATION: n = A,T,C or G
<220> FEATURE:
<221> NAME/KEY: misc_feature
<222> LOCATION: 1475
<223> OTHER INFORMATION: n = A,T,C or G

<400> SEQUENCE: 5
ggcacgagcc tagttaaaac tttaactatg tctttccata tcagtcaccc ggctgaatct      60
tcctcctcat attcaccaca accgtgccgt caatttacct tttcggagat tcaacttgca     120
acccaaaact tgatgagtc gttggtgata ggacgtgggg ggtttggcaa ggtttacaga     180
ggaaccttca cttatgggga acatacttg gatgctgcaa ttaagcgact ggaatcaggt     240
tctagtcaag gagcggtaga gtttagggct gaaattgaga tgctctcaaa tctaaggcac     300
tgtcatttgg tgtctttaat tggttactgt agtgatgggc aagagatggt tcttgtatat     360
gaacatatgc ccaatggaac tcttgcagat cgtctccaca agcgtcgagc tcctctaact     420
tgggtaagaa gactcaaaat atgcataggg gccgctcgtg gtttagatta cttgcacact     480
ggtacgggta ttaaccatgg agttatacat cgggatgtta agagcacaaa tatattgtta     540
gatgacaatt gggcagctaa ggttctgac tttggtttgt ccaaaattgg tccaacaaat     600
cagccttcaa cttatgttaa cactttggtg agaggcacct ttggatatat ggatccagat     660
tactttcaaa caggtaggct gactcgaaag tctgacgtgt atgcctttgg ggtggtcctg     720
tttgaagtcc tatgtgggaa acaagtagta ctgatgagga gcactggggt ttggcaacat     780
gggctcaaga ctctcttaaa gaaggaaggc taaagcaaat gttgattct aatttaaggg     840 ggagaatatc cccaaaatgt ttgaaggagt ttgcactact agctgaccgg tgtttgcata     900
gccgtcccaa gcaacgtcct gcaatggcgg aggttgtgat tggtcttgag tcaatcctag     960
ccttacagga gaaaccgag agtacatggg taccaacatt tctctttcca tccacttggg    1020
aaaagacagt tggaggtaca gatttaaaat ccctggaacg atacctctac aatgttggag    1080
gtgaagacaa aatagtacac aagtttgatt ttataacgat tcttgatgca actgaaaact    1140
```

-continued

```
tctctgaagc taataagatt tcatcctgct catatgattc cgtgtacaag ggacggctac    1200
aaaatggaca agatataaca gtcactcaat attcaaaagc ctccacatat aaactgtgta    1260
tgaatgaagc atcaatactt gtaaaggttg aacatcaaaa tttgattcag ttgcttggat    1320
attgcattca cggaacagaa gtgtacctca tctatgactt tccacttaat gcaactatgg    1380
ctgacatgat ttatgatcct agtgtaatct tttggactgg ataaacggta caaaataatc    1440
ctagacatag ccagagcact tgtatatctt cacangcatg ctccattcgg atcatacatc    1500
ttgatgtaaa cccgcaacat tctatagatg aagttatacc cagctgtcag gtttggggag    1560
cagtgacacc agtgagacag attgcgtttc tcttgataat gtctttggga ctatgggata    1620
cattgcacct gaatatcata ggacattacg ttgctcaact aaggcagatg tctatagttt    1680
tggtgtgttg attttgaaa cagtaactgg aaaaccata cagaatttat tatctctagc     1740
tttagacaag caccttggtt ttgcagacta tatccacaaa aattggttgg aagggacatt    1800
gtcagatata attgatcccc aaattgatgc tgattcagtt tcgatgacta aattcgtgga    1860
gattgggttg ttgtgtgttc aaggattagc agcggatagg ccaacaatgg aggaggttat    1920
tggcatgttg cttggcacct cgtctctaac ttttcatgtg tcggaaatgc gagaaaggat    1980
gatgtttaat ggcgtgacta catatttata taatatgaaa gtgaaaggtc ggtggtaata    2040
agacaaaaca ccgaccaaat tacaaaactg ccctaataa atttatttta ttgtgccaaa    2100
aaaaaaaaaa aaaa                                                      2114
```

<210> SEQ ID NO 6
<211> LENGTH: 850
<212> TYPE: DNA
<213> ORGANISM: Helianthus annuus

<400> SEQUENCE: 6

```
cttgctactg aacctcgttg tgggtttctg caaattcatc ttttttcacc acaaattgtt     60
aaaaaaagat ttttttttt ttttaattta attgtggcat agttaactgt gaaacttggt    120
tccagtgcaa aagattgccc catatctttc tttcatgtga taaaacagag ttgcatgtta    180
tctcttttca cctttttcac aacacccaga tcagatctgc ttttctttt ataaaatctt    240 gttgtttcaa gaatcttgtt gaagtgaaaa aagacaccca ctttcaagaa taataataat    300
catttcaatg ggtatttgtt tgagtgctag aatcaaagct gaaagcccat atcacacagg    360
ggtgagttca agaactggaa gtacagaagg aaatgataat ggtaattcaa gtggcagcaa    420
ctgcaaccct ccgatccccc ggagcgaagg tgaaatcttg caatcttgta acttgaagag    480 tttaattat tcggatcttc gaatggctac gagaaatttt cggcccgata gcgtgttggg    540
cgaaggtggg ttcgggtcgg tttataaagg gtggatcgat gaacaatcgt tcgccgcttc    600
aaaaccgggg tctggagtcg ttgttgctgt caaaagactt aatgcagaaa gttttcaagg    660
tcacagagaa tggctggcgg aagtgaacta tttagggcag ttttcgcacc cgaatctcgt    720
gaatttgatt gggtattgtt tggaagacga acatcggctt ctagtttacg agttcatgcc    780
acgaggcagc ttggagaatc acttgttcag gaaaggatct tattttcaac cgctaacatg    840
gagtctccga                                                          850
```

<210> SEQ ID NO 7
<211> LENGTH: 2594
<212> TYPE: DNA
<213> ORGANISM: Helianthus annuus
<220> FEATURE:

<221> NAME/KEY: CDS
<222> LOCATION: (21)...(1733)

<400> SEQUENCE: 7

```
ctctcgcatc tgctgcctat atg gaa att tct cac cta ttc gaa ggt tgt tgt        53
                     Met Glu Ile Ser His Leu Phe Glu Gly Cys Cys
                      1               5                  10 ctt ctt gaa aat att cgt gag gaa tca agc aaa cag ggt ttg aaa aag        101
Leu Leu Glu Asn Ile Arg Glu Glu Ser Ser Lys Gln Gly Leu Lys Lys
            15                  20                  25 ttg caa gaa aat ttt ctc tca ctt gtt ttg aaa acc gat gtg aag gta        149
Leu Gln Glu Asn Phe Leu Ser Leu Val Leu Lys Thr Asp Val Lys Val
        30                  35                  40 ggg aat gag ata ata gga agg agc atg ata aaa agt agg cta tct cac        197
Gly Asn Glu Ile Ile Gly Arg Ser Met Ile Lys Ser Arg Leu Ser His
    45                  50                  55 aaa agg ttt tta gtt gtt ctc gat gat gtt gat aat ttt gag caa ctt        245
Lys Arg Phe Leu Val Val Leu Asp Asp Val Asp Asn Phe Glu Gln Leu
 60                  65                  70                  75 gag gcg ttg gcg gga tcc cac gat tgg ttt ggt gag ggg agc cgg ata        293
Glu Ala Leu Ala Gly Ser His Asp Trp Phe Gly Glu Gly Ser Arg Ile
                 80                  85                  90 ata att acg act aga gat gtg cat ttg cta tcc agc agg gcg caa acg        341
Ile Ile Thr Thr Arg Asp Val His Leu Leu Ser Ser Arg Ala Gln Thr
             95                 100                 105 att tat gaa gtg aat ttg tta tca caa gat gaa gca atc aag ctc tta        389
Ile Tyr Glu Val Asn Leu Leu Ser Gln Asp Glu Ala Ile Lys Leu Leu
        110                 115                 120 aaa aga tat gca tac cat aaa gat aaa cct gtt gaa gag tat gag atg        437
Lys Arg Tyr Ala Tyr His Lys Asp Lys Pro Val Glu Glu Tyr Glu Met
125                 130                 135 ctt gca gaa gag gta gtt tct tat gct ggt ggg ctc cca cta gcg ctt        485
Leu Ala Glu Glu Val Val Ser Tyr Ala Gly Gly Leu Pro Leu Ala Leu
140                 145                 150                 155 aaa gtt cta ggt tcg ttt cta tat ggc aaa gac aag gat gag tgg aag        533
Lys Val Leu Gly Ser Phe Leu Tyr Gly Lys Asp Lys Asp Glu Trp Lys
                160                 165                 170 agt acg ttg gcc aag tta aaa tgc atc ccg gaa gag aag gtc atg gag        581
Ser Thr Leu Ala Lys Leu Lys Cys Ile Pro Glu Glu Lys Val Met Glu
            175                 180                 185 aga ctc aaa ata agt tat gat gga ctt gaa ccc tac cag aaa gag tta        629
Arg Leu Lys Ile Ser Tyr Asp Gly Leu Glu Pro Tyr Gln Lys Glu Leu
        190                 195                 200 ttc tta gat att gca tgt ttc atg agg aga tgg tgg tta caa tcg gtt        677
Phe Leu Asp Ile Ala Cys Phe Met Arg Arg Trp Trp Leu Gln Ser Val
    205                 210                 215 ttg gat cgt gca atg atg gtg ctt gat gct tgt aat ttg cac cct gtt        725
Leu Asp Arg Ala Met Met Val Leu Asp Ala Cys Asn Leu His Pro Val
220                 225                 230                 235 ata ggg tta aag gtg ttg gaa caa aaa tcc ctc ata aaa gtt tca aaa        773
Ile Gly Leu Lys Val Leu Glu Gln Lys Ser Leu Ile Lys Val Ser Lys
                240                 245                 250 aaa gga aga ttt gag atg cat gac ttg ata gaa gaa atg gcc cac tac        821
Lys Gly Arg Phe Glu Met His Asp Leu Ile Glu Glu Met Ala His Tyr
            255                 260                 265 att gtt aga ggg gaa cac cct aat aat cct gaa aag cat agc agg att        869
Ile Val Arg Gly Glu His Pro Asn Asn Pro Glu Lys His Ser Arg Ile
        270                 275                 280 tgg aat agg gaa gat ttg gaa gag ctt tgt gct atg gga gca gct gca        917
Trp Asn Arg Glu Asp Leu Glu Glu Leu Cys Ala Met Gly Ala Ala Ala
```

```
          285                 290                  295
ccc tca atg gaa aat gaa gta tta gct aat ttg cca atg tat ata att        965
Pro Ser Met Glu Asn Glu Val Leu Ala Asn Leu Pro Met Tyr Ile Ile
300                 305                 310                 315 agc cat cca ggt cta cta ctt gat gtt gtt cca aac atg aag aac ctt       1013
Ser His Pro Gly Leu Leu Leu Asp Val Val Pro Asn Met Lys Asn Leu
                320                 325                 330 cga tgg ata atg ttg att ggt cat ggg gat ccg tca tct tca ttc cca       1061
Arg Trp Ile Met Leu Ile Gly His Gly Asp Pro Ser Ser Ser Phe Pro
                335                 340                 345 tca aat ttt cag cca aca aag ctt cgt tgt cta atg ttg ata gag agc       1109
Ser Asn Phe Gln Pro Thr Lys Leu Arg Cys Leu Met Leu Ile Glu Ser
            350                 355                 360 aag caa aaa gaa ctc tgg gaa ggg tgt aag agt cta cca aat ttg aaa       1157
Lys Gln Lys Glu Leu Trp Glu Gly Cys Lys Ser Leu Pro Asn Leu Lys
365                 370                 375 att ctt gat ctc tcg ggt tca agt aac cta atc aag aca cca gat ttt       1205
Ile Leu Asp Leu Ser Gly Ser Ser Asn Leu Ile Lys Thr Pro Asp Phe
380                 385                 390                 395 gaa ggc ctt cca tgt ctt gaa aga ttg att tta aaa tat tgt gag aga       1253
Glu Gly Leu Pro Cys Leu Glu Arg Leu Ile Leu Lys Tyr Cys Glu Arg
                400                 405                 410 tta gaa gag att cat cca tca att gga tat cac aaa agg ctt gtt tac       1301
Leu Glu Glu Ile His Pro Ser Ile Gly Tyr His Lys Arg Leu Val Tyr
                415                 420                 425 gtg aac atg aaa ggg tgt gca aga ctt aaa agg ttt cca ccc atc ata       1349
Val Asn Met Lys Gly Cys Ala Arg Leu Lys Arg Phe Pro Pro Ile Ile
                430                 435                 440 cac atg aaa aaa ttg gag act ctt aat ctc agt gat tgc agt aaa ctt       1397
His Met Lys Lys Leu Glu Thr Leu Asn Leu Ser Asp Cys Ser Lys Leu
            445                 450                 455 caa cag ttt ccg gat atc cag tca aac atg gat agc ttg gta acc att       1445
Gln Gln Phe Pro Asp Ile Gln Ser Asn Met Asp Ser Leu Val Thr Ile
460                 465                 470                 475 gat ctg cat aat act ggt ata gaa ata atc cca ccg tca gtt gga cga       1493
Asp Leu His Asn Thr Gly Ile Glu Ile Ile Pro Pro Ser Val Gly Arg
                480                 485                 490 ttt tgt acc aac ctt gtt tct tta gat tta agt caa tgt tac aaa ctg       1541
Phe Cys Thr Asn Leu Val Ser Leu Asp Leu Ser Gln Cys Tyr Lys Leu
                495                 500                 505 aaa agg ata gag gac agc ttt cat ctc tta aaa agt ttg aaa gac ctg       1589
Lys Arg Ile Glu Asp Ser Phe His Leu Leu Lys Ser Leu Lys Asp Leu
                510                 515                 520 aat ctc agt tgt tgt ttt ggg tta caa tct ttt cgt caa gac cgg ttg       1637
Asn Leu Ser Cys Cys Phe Gly Leu Gln Ser Phe Arg Gln Asp Arg Leu
525                 530                 535 gtg agc ctc aag cta cct cag ttt cca cgt ttt cta agg aaa tta aat       1685
Val Ser Leu Lys Leu Pro Gln Phe Pro Arg Phe Leu Arg Lys Leu Asn
540                 545                 550                 555 ctt aga ggc tgc aga ttg gaa gat gga ggc atc cca tct gat ata ttt       1733
Leu Arg Gly Cys Arg Leu Glu Asp Gly Gly Ile Pro Ser Asp Ile Phe
                560                 565                 570 taattgccag acctcccatc aagcatagct attctcaaag caaaaggttg tgactcactt       1793
gaaattgtaa gagatttatc agactataaa tggttgtgga aagtctcact ttggaggaga       1853
gcgaataaga gggtactact ttatatgctt gaggaaaatg cagttaaaga agatcgcttt       1913
atgagcgtgt taagtcccaa tgttcaacca tcaagcattt ataccaaact tgtcacattg       1973
caacttccac acaactggta tagtgacttt agtggatttt tattatcatt aggtgaccgt       2033
```

```
tatgggacgt accgcatagt aattaagcag gagatgtcca ccgatcactc tgaaaagtct    2093
gatgaagatc gggaacaacg taactatgaa agggtgggtt acgtacccct tagttcattg    2153
aggcacatcc catggttcaa tcctacatac cctaaaaata tttcatttca aataatggat    2213
aaatatggta atacgaagaa aattggtctt aatgtagaac ttgttcgtag taaaagtaaa    2273
atatgtgatt taaacgaaca cccaatcgat tactcagagt gttgggatga agaatataaa    2333
gatacaaaga cctttgacat cgtatatgat tcaaagtcct ctgaaattca gatttcatgg    2393
gaacatccgt agtcgatctc agtttcaaat ttcaacattt gcccacattt tgttaccatt    2453
ctaagtttgc ttttgtttca ccaacatcat tgcgacctga agaagttgt aataaatgtt    2513 cctctattaa ctcttaagac ttcacattct atactttgtt cattaccagg ttaaaaaaaa    2573
aaaaaaaaaa aaaaaaaaa a                                                2594
```

<210> SEQ ID NO 8
<211> LENGTH: 571
<212> TYPE: PRT
<213> ORGANISM: Helianthus annuus

<400> SEQUENCE: 8

```
Met Glu Ile Ser His Leu Phe Glu Gly Cys Cys Leu Leu Glu Asn Ile
1               5                   10                  15

Arg Glu Glu Ser Ser Lys Gln Gly Leu Lys Lys Leu Gln Glu Asn Phe
            20                  25                  30

Leu Ser Leu Val Leu Lys Thr Asp Val Lys Val Gly Asn Glu Ile Ile
        35                  40                  45

Gly Arg Ser Met Ile Lys Ser Arg Leu Ser His Lys Arg Phe Leu Val
    50                  55                  60

Val Leu Asp Asp Val Asp Asn Phe Glu Gln Leu Glu Ala Leu Ala Gly
65                  70                  75                  80

Ser His Asp Trp Phe Gly Glu Gly Ser Arg Ile Ile Thr Thr Arg
                85                  90                  95

Asp Val His Leu Leu Ser Ser Arg Ala Gln Thr Ile Tyr Glu Val Asn
            100                 105                 110

Leu Leu Ser Gln Asp Glu Ala Ile Lys Leu Leu Lys Arg Tyr Ala Tyr
        115                 120                 125

His Lys Asp Lys Pro Val Glu Glu Tyr Glu Met Leu Ala Glu Glu Val
    130                 135                 140

Val Ser Tyr Ala Gly Gly Leu Pro Leu Ala Leu Lys Val Leu Gly Ser
145                 150                 155                 160

Phe Leu Tyr Gly Lys Asp Lys Asp Glu Trp Lys Ser Thr Leu Ala Lys
                165                 170                 175

Leu Lys Cys Ile Pro Glu Glu Lys Val Met Glu Arg Leu Lys Ile Ser
            180                 185                 190

Tyr Asp Gly Leu Glu Pro Tyr Gln Lys Glu Leu Phe Leu Asp Ile Ala
        195                 200                 205

Cys Phe Met Arg Arg Trp Trp Leu Gln Ser Val Leu Asp Arg Ala Met
    210                 215                 220

Met Val Leu Asp Ala Cys Asn Leu His Pro Val Ile Gly Leu Lys Val
225                 230                 235                 240

Leu Glu Gln Lys Ser Leu Ile Lys Val Ser Lys Gly Arg Phe Glu
                245                 250                 255

Met His Asp Leu Ile Glu Glu Met Ala His Tyr Ile Val Arg Gly Glu
            260                 265                 270
```

His Pro Asn Asn Pro Glu Lys His Ser Arg Ile Trp Asn Arg Glu Asp
            275                 280                 285

Leu Glu Glu Leu Cys Ala Met Gly Ala Ala Pro Ser Met Glu Asn
        290                 295                 300

Glu Val Leu Ala Asn Leu Pro Met Tyr Ile Ile Ser His Pro Gly Leu
305                 310                 315                 320

Leu Leu Asp Val Val Pro Asn Met Lys Asn Leu Arg Trp Ile Met Leu
                325                 330                 335

Ile Gly His Gly Asp Pro Ser Ser Phe Pro Ser Asn Phe Gln Pro
            340                 345                 350

Thr Lys Leu Arg Cys Leu Met Leu Ile Glu Ser Lys Gln Lys Glu Leu
            355                 360                 365

Trp Glu Gly Cys Lys Ser Leu Pro Asn Leu Lys Ile Leu Asp Leu Ser
    370                 375                 380

Gly Ser Ser Asn Leu Ile Lys Thr Pro Asp Phe Glu Gly Leu Pro Cys
385                 390                 395                 400

Leu Glu Arg Leu Ile Leu Lys Tyr Cys Glu Arg Leu Glu Glu Ile His
                405                 410                 415

Pro Ser Ile Gly Tyr His Lys Arg Leu Val Tyr Val Asn Met Lys Gly
            420                 425                 430

Cys Ala Arg Leu Lys Arg Phe Pro Pro Ile Ile His Met Lys Lys Leu
        435                 440                 445

Glu Thr Leu Asn Leu Ser Asp Cys Ser Lys Leu Gln Gln Phe Pro Asp
    450                 455                 460

Ile Gln Ser Asn Met Asp Ser Leu Val Thr Ile Asp Leu His Asn Thr
465                 470                 475                 480

Gly Ile Glu Ile Ile Pro Pro Ser Val Gly Arg Phe Cys Thr Asn Leu
                485                 490                 495

Val Ser Leu Asp Leu Ser Gln Cys Tyr Lys Leu Lys Arg Ile Glu Asp
            500                 505                 510

Ser Phe His Leu Leu Lys Ser Leu Lys Asp Leu Asn Leu Ser Cys Cys
        515                 520                 525

Phe Gly Leu Gln Ser Phe Arg Gln Asp Arg Leu Val Ser Leu Lys Leu
    530                 535                 540

Pro Gln Phe Pro Arg Phe Leu Arg Lys Leu Asn Leu Arg Gly Cys Arg
545                 550                 555                 560

Leu Glu Asp Gly Gly Ile Pro Ser Asp Ile Phe
            565                 570

<210> SEQ ID NO 9
<211> LENGTH: 2793
<212> TYPE: DNA
<213> ORGANISM: Helianthus annuus

<400> SEQUENCE: 9
acgagcagcc atgaagcaaa atgcatcagt gacattgttg gtacaatttc ttctaggctt    60
tcttcactaa atacaaacga taataaagac ctcatcggaa tagagacccg cttacaagat   120
cttatatcaa agttggaaat cgagtcaggt ggtgtgcgca tggttggaat atggggagtt   180
gggggtggtg gtaagactac tctcgcatct gctgcctata tggaaatttc tcacctattc   240
gaaggttgtt gtcttcttga aaatattcgt gaggaatcaa gcaaacaggg tttgaaaaag   300
ttgcaagaaa attttctctc acttgttttg aaaaccgatg tgaaggtagg gaatgagata   360
ataggaagga gcatgataaa aagtaggcta tctcacaaaa ggttttttagt tgttctcgat   420

```
gatgttgata attttgagca acttgaggcg ttggcgggat cccacgattg gtttggtgag      480
gggagccgga taataattac gactagagat gtgcatttgc tatccagcag ggcgcaaacg      540
atttatgaag tgaatttgtt atcacaagat gaagcaatca agctcttaaa aagatatgca      600
tatcataaag ataaacctgt tgaagagtat gagatgcttg cagaagaggt agtttcttat      660
gctggtgggc tcccactagc gcttaaagtt ctaggttcgt ttctatatgg caaagacaag      720
gatgagtgga agagtacgtt ggccaagtta aaatgcatcc cggaagagaa ggtcatggag      780
agactcaaaa taagttatga tggacttgaa ccctaccaga aagagttatt cttagatatt      840
gcatgtttca tgaggagatg gtggttacaa tcggttttgg atcgtgcaat gatggtgctt      900
gatgcttgta atttgcaccc tgttataggg ttaaaggtgt tggaacaaaa atccctcata      960
aaagtttcaa aaaaggaag atttgagatg catgacttga tagaagaaat ggcccactac     1020
attgttagag gggaacaccc taataatcct gaaaagcata gcaggatttg aatagggaa     1080 gatttggaag agctttgtgc tatgggagca gctgcaccct caatggaaaa tgaagtatta     1140
gctaatttgc caatgtatat aattagccat ccaggtctac tacttgatgt tgttccaaac     1200
atgaagaacc ttcgatggat aatgttgatt ggtcatgggg atccgtcatc ttcattccca     1260
tcaaattttc agccaacaaa gcttcgttgt ctaatgttga tagagagcaa gcaaaaagaa     1320
ctctgggaag ggtgtaagag tctaccaaat ttgaaaattc ttgatctctc gggttcaagt     1380
aacctaatca agacaccaga ttttgaaggc cttccatgtc ttgaaagatt gattttaaaa     1440
tattgtgaga gattagaaga gattcatcca tcaattggat atcacaaaag gcttgtttac     1500
gtgaacatga agggtgtgc aagacttaaa aggtttccac ccatcataca catgaaaaaa     1560
ttggagactc ttaatctcag tgattgcagt aaacttcaac agtttccgga tatccagtca     1620
aacatggata gcttggtaac cattgatctg cataatactg gtatagaaat aatcccaccg     1680
tcagttggac gattttgtac caaccttgtt tctttagatt taagtcaatg ttacaaactg     1740
aaaaggatag aggacagctt tcatctctta aaaagtttga aagacctgaa tctcagttgt     1800
tgttttgggt tacaatcttt tcgtcaagac cggttggtga gcctcaagct acctcagttt     1860
ccacgttttc taaggaaatt aaatcttaga ggctgcagat tggaagatgg aggcatccca     1920
tctgatatat tttaattgcc agacctccca tcaagcatag ctattctcaa agcaaaaggt     1980
tgtgactcac ttgaaattgt aagagattta tcagactata atggttgtg aaagtctca     2040 ctttggagga gagcgaataa gagggtacta ctttatatgc ttgaggaaaa tgcagttaaa     2100
gaagatcgct ttatgagcgt gttaagtccc aatgttcaac catcaagcat ttataccaaa     2160
cttgtcacat tgcaacttcc acacaactgg tatagtgact tagtggatt tttattatca     2220 ttaggtgacc gttatgggac gtaccgcata gtaattaagc aggagatgtc caccgatcac     2280
tctgaaaagt ctgatgaaga tcgggaacaa cgtaactatg aawsrgtggg ttacgtaccc     2340
tttagttcat tgaggcacat cccatggttc aatcctacat accctaaaaa tatttcattt     2400
caaataatgg ataaatatgg taatacgaag aaaattggtc ttaatgtaga acttgttcgt     2460
agtaaaagta aaatatgtga tttaaacgaa cacccaatcg attactcaga gtgttgggat     2520
gaagaatata aagatacaaa gacctttgac atcgtatatg attcaaagtc ctctgaaatt     2580
cagatttcat gggaacatcc gtagtcgatc tcagtttcaa atttcaacat ttgcccacat     2640
tttgttacca ttctaagttt gcttttgttt caccaacatc attgcgacct gaagaagttt     2700
gtaataaatg ttcctctatt aactcttaag acttcacatt ctatactttg ttcattacca     2760
```

-continued

```
ggttaaaaaa aaaaaaaaaa aaaaaaaaaa aaa                                    2793

<210> SEQ ID NO 10
<211> LENGTH: 670
<212> TYPE: DNA
<213> ORGANISM: Helianthus annuus

<400> SEQUENCE: 10
acgagcagcc atgaagcaaa atgcatcagt gacattgttg gtacaatttc ttctaggctt         60
tcttcactaa atacaaacga taataaagac ctcatcggaa tagagacccg cttacaagat        120
cttatatcaa agttggaaat cgagtcaggt ggtgtgcgca tggttggaat atggggagtt        180
gggggtggtg gtaagactac tctcgcatct gctgcctata tggaaatttc tcacctattc        240
gaaggttgtt gtcttcttga aaatattcgt gaggaatcaa gcaaacaggg tttgaaaaag        300
ttgcaagaaa attttctctc acttgttttg aaaaccgatg tgaaggtagg gaatgagata        360
ataggaagga gcatgataaa aagtaggcta tctcacaaaa ggttttagt tgttctcgat         420 gatgttgata ttttgagca acttgaggcg ttggcgggat cccacgattg gtttggtgag         480
gggagccgga taataattac gactagagat gtgcatttgc tatccagcag ggcgcaaacg        540
atttatgaag tgaatttgtt atcacaagat gaagcaatca agctcttaaa aagatatgca        600
tatcataaag ataaacctgt tgaagagtat gagatgcttg cagaagaggt agtttcttat        660
gctggtgggc                                                              670

<210> SEQ ID NO 11
<211> LENGTH: 1200
<212> TYPE: DNA
<213> ORGANISM: Helianthus annuus

<400> SEQUENCE: 11 atg cag aaa tct ctc acc gat ttg aag gtc act gcc ttc ttc aaa ata          48 tcc gtg agg gag tca aac aag cat ggt ttg gaa aag cta caa gaa aaa          96 ttt ctc tca ctc att ttg aaa gca gat gtg aag gta ggg aat gag ata         144 gaa gga aga agc att ata gaa aga agg tta cgt aat aaa agc gta tta         192 gtt gtt ctt gac gat gtt gat gac cat aag caa cta gag gct cta gcc         240 gga tca cat gct tgg ttt ggt aag ggg agc agg ata ata att acg acg         288 agg gat gag cat ttg cta acc cgc cat gca gac atg ata tat gaa gtg         336 agt ttg tta tca cat gac gag gct atg gag ctc ttc aac aaa cat gca         384 tat cgg aaa gat aaa cct ata gaa gat tac gag atg ctt tca aac gat         432 gta gtt tct tat gct agt ggg ctc cca tta gca ctt gaa att cta ggt         480 tct ttt cta tat gac aaa aac aag gat gag tgg aag agt gca ttg gca         528 agt taa aat gca tcc caa atg tta aag tca ccg aaa gac tca aaa taa         576 gtt atg atg gac ttg aac ccg acc atc aaa aaa ata ttc tta gat att         624 gct tgt ttt tgg agg aga caa cac atg gat gag gca atg atg gtg ctt         672 gat gct tgt aat tta cac cct tgt ata ggg gtg aag gtg ttg att caa         720 aaa tct ctc ata aaa gtt tca gat gat gta ttt ggt gat aaa ata gtt         768 gat atg cat gac ttg gtg gaa gaa atg gct cac tac att gtt aga ggg         816 gca cac cct aat cat cct gaa aag cat agt aga att tgg aag gag gag         864 gat ata gca tac ctc tgt gat atg ggg gca gat gca gtg cca atg gaa         912
```

-continued

```
act gaa gta gaa gct ttg tgt tct tat gat gtt ccg gat cta tct gat        960 gtg gtt gca aac atg aag aaa ctt cgg tgg att cgt ttt gat cag tat       1008 cag aca tct tca ttc cca tca aat ttt cag cca aca gag ctt tgt tgt       1056 cta gag ttg cat aag agc caa caa aaa gaa ctg tgg cat ggg tat aag       1104 ctt cta cca aat ttg aaa att ctt gat ctt agg aga tca tca aaa cta       1152 atc acg aca cca aaa ttt tga tgg cct tcc atg tct gaa aag att gat       1200
```

<210> SEQ ID NO 12
<211> LENGTH: 3456
<212> TYPE: DNA
<213> ORGANISM: Helianthus annuus
<220> FEATURE:
<221> NAME/KEY: CDS
<222> LOCATION: (15)...(1442)
<220> FEATURE:
<221> NAME/KEY: misc_feature
<222> LOCATION: (1)...(3456)
<223> OTHER INFORMATION: n = A,T,C or G
<220> FEATURE:
<221> NAME/KEY: misc_feature
<222> LOCATION: 3427
<223> OTHER INFORMATION: n = A,T,C or G
<220> FEATURE:
<221> NAME/KEY: misc_feature
<222> LOCATION: 3427
<223> OTHER INFORMATION: n = A,T,C or G

<400> SEQUENCE: 12

```
ggcacgagtg aaca atg gct gtt gga ctt atg gag act ctg aaa gaa gct         50
              Met Ala Val Gly Leu Met Glu Thr Leu Lys Glu Ala
               1               5                  10 ata acc gcc tac acc gga ctc tct ccc act act ttc ttc act gtt ctc         98
Ile Thr Ala Tyr Thr Gly Leu Ser Pro Thr Thr Phe Phe Thr Val Leu
 15                  20                  25 gcc gcc ggt gtc acc gtc tac tac atc gtt tcc gtt ctg ttc atg aga        146
Ala Ala Gly Val Thr Val Tyr Tyr Ile Val Ser Val Leu Phe Met Arg
         30                  35                  40 ggc tcc tcc gat cac cat caa caa cac agc caa atg tct tcc gaa gaa        194
Gly Ser Ser Asp His His Gln Gln His Ser Gln Met Ser Ser Glu Glu
 45                  50                  55                  60 gac aga tca gcg gca tct tct tcg tcc gct tct cac tca att tct gcc        242
Asp Arg Ser Ala Ala Ser Ser Ser Ser Ala Ser His Ser Ile Ser Ala
             65                  70                  75 tct act tct caa tca tgg aat cat gat gta ttt ctg agc ttt cgg gga        290
Ser Thr Ser Gln Ser Trp Asn His Asp Val Phe Leu Ser Phe Arg Gly
         80                  85                  90 gaa gac acc cgt aat agc ttt gtg gat cat ctc tat gcg gct ctt gca        338
Glu Asp Thr Arg Asn Ser Phe Val Asp His Leu Tyr Ala Ala Leu Ala
     95                 100                 105 caa caa gga atc cag gcg tac aag gat gac gaa aca ctt cct cgg ggt        386
Gln Gln Gly Ile Gln Ala Tyr Lys Asp Asp Glu Thr Leu Pro Arg Gly
110                 115                 120 gag cga atc ggt cca gcc ctc ttg aaa gct atc caa gaa tca cgc atc        434
Glu Arg Ile Gly Pro Ala Leu Leu Lys Ala Ile Gln Glu Ser Arg Ile
125                 130                 135                 140 gcc gtt gtt gtg ttc tct caa aac tat gcg gat tca tct tgg tgc ttg        482
Ala Val Val Val Phe Ser Gln Asn Tyr Ala Asp Ser Ser Trp Cys Leu
                145                 150                 155 gac gag ctt gca cat att atg gag tgc atg gac acg aga ggg cag atc        530
Asp Glu Leu Ala His Ile Met Glu Cys Met Asp Thr Arg Gly Gln Ile
            160                 165                 170
```

-continued

| | |
|---|---|
| gtg att ccc ata ttt tat ttt gta gat cca tcg gat gtt aga aaa caa<br>Val Ile Pro Ile Phe Tyr Phe Val Asp Pro Ser Asp Val Arg Lys Gln<br>        175                   180                  185 | 578 |
| aag ggg aaa tat gga aaa gca ttt aga aaa cgt aag agg gaa aat agg<br>Lys Gly Lys Tyr Gly Lys Ala Phe Arg Lys Arg Lys Arg Glu Asn Arg<br>        190                   195                  200 | 626 |
| caa aaa gtt gaa tca tgg aga aaa gct ctg gaa aag gct ggc aat ctt<br>Gln Lys Val Glu Ser Trp Arg Lys Ala Leu Glu Lys Ala Gly Asn Leu<br>205                  210                  215                  220 | 674 |
| tct gga tgg gtc atc aat gaa aac agt cac gaa gca aaa tgc atc aaa<br>Ser Gly Trp Val Ile Asn Glu Asn Ser His Glu Ala Lys Cys Ile Lys<br>                       225                   230                  235 | 722 |
| gaa att gtt gct aca att tct agt agg ctg cct aca cta agt aca aac<br>Glu Ile Val Ala Thr Ile Ser Ser Arg Leu Pro Thr Leu Ser Thr Asn<br>        240                   245                  250 | 770 |
| gtc aat aaa gac ctc att gga ata gag aca cgc tta caa gat ctg aaa<br>Val Asn Lys Asp Leu Ile Gly Ile Glu Thr Arg Leu Gln Asp Leu Lys<br>                       255                   260                  265 | 818 |
| tca aag ttg aaa atg gag tca ggt gat gta cgc att att gga ata tgg<br>Ser Lys Leu Lys Met Glu Ser Gly Asp Val Arg Ile Ile Gly Ile Trp<br>        270                   275                  280 | 866 |
| gga gtt ggg ggt ggt ggt aag act act ctc gca tct gct gct tat gcg<br>Gly Val Gly Gly Gly Gly Lys Thr Thr Leu Ala Ser Ala Ala Tyr Ala<br>285                  290                  295                  300 | 914 |
| gaa atc tct cgc cga ttt gaa gct cac tgc ctt ctt caa aat atc cgt<br>Glu Ile Ser Arg Arg Phe Glu Ala His Cys Leu Leu Gln Asn Ile Arg<br>                       305                   310                  315 | 962 |
| gag gag tca aac aag cat ggt ttg gaa aaa cta caa gaa aaa att ctc<br>Glu Glu Ser Asn Lys His Gly Leu Glu Lys Leu Gln Glu Lys Ile Leu<br>        320                   325                  330 | 1010 |
| tca ctt gtt ttg aaa aca aaa gat gtt gtg gta ggg agt gag ata gaa<br>Ser Leu Val Leu Lys Thr Lys Asp Val Val Val Gly Ser Glu Ile Glu<br>335                  340                  345 | 1058 |
| gga aga agc atg ata gaa aga agg tta cgt aat aaa agc gta tta gtt<br>Gly Arg Ser Met Ile Glu Arg Arg Leu Arg Asn Lys Ser Val Leu Val<br>        350                   355                  360 | 1106 |
| gtt ctt gac gat gtt gat gac ctc aag caa cta gag gct cta gcc gga<br>Val Leu Asp Asp Val Asp Asp Leu Lys Gln Leu Glu Ala Leu Ala Gly<br>365                  370                  375                  380 | 1154 |
| tca cat gct tgg ttt ggt aag ggg agc agg ata ata att acg acg agg<br>Ser His Ala Trp Phe Gly Lys Gly Ser Arg Ile Ile Ile Thr Thr Arg<br>                       385                   390                  395 | 1202 |
| gat gag cat ttg cta acc cgc cat gca gac atg ata tat gaa gtg agt<br>Asp Glu His Leu Leu Thr Arg His Ala Asp Met Ile Tyr Glu Val Ser<br>        400                   405                  410 | 1250 |
| ttg tta tca cat gac gag gct atg gag ctc ttc aac aaa cat gca tat<br>Leu Leu Ser His Asp Glu Ala Met Glu Leu Phe Asn Lys His Ala Tyr<br>415                  420                  425 | 1298 |
| cgg aaa gat aaa cct ata gaa gat tac gag atg ctt tca aac gat gta<br>Arg Lys Asp Lys Pro Ile Glu Asp Tyr Glu Met Leu Ser Asn Asp Val<br>        430                   435                  440 | 1346 |
| gtt tct tat gct agt ggg ctc cca tta gca ctt gaa att cta ggt tct<br>Val Ser Tyr Ala Ser Gly Leu Pro Leu Ala Leu Glu Ile Leu Gly Ser<br>445                  450                  455                  460 | 1394 |
| ttt cta tat gac aaa aac aag gat gag tgg aag agt gca ttg gca agt<br>Phe Leu Tyr Asp Lys Asn Lys Asp Glu Trp Lys Ser Ala Leu Ala Ser<br>                       465                   470                  475 | 1442 |
| taaaatgcat cccaaatgtt aaagtcaccg aaagactcaa aataagttat gatggacttg | 1502 |

-continued

```
aacccaacat caaaaaatat cctaaataat gctgtttgga ggaacacaca tggatgaggc    1562
atgatgggct tgagctggaa ttacaccctg gtaagtggaa gggttttcaa accccaaaat    1622 gttataqggt taaggtgtt ggaacaaaaa tccctcataa aagtttcaaa aaaaggaaga    1682
tttgagatgc atgacttgat agaagaaatg gcccactaca ttgttagagg ggaacaccct    1742
aataatcctg aaaagcatag caggatttgg aataggaag attttggaaga gctttgtgct    1802 atgggagcag ctgcaccctc aatggaaaat gaagtattag ctaatttgcc aatgtatata    1862
attagccatc caggtctact acttgatgtt gttccaaaca tgaagaacct tcgatggata    1922
atgttgattg gtcatgggga tccgtcatct tcattcccat caaatttttca gccaacaaag    1982 cttcgttgtc tctaatcacg acaccaaatt ttgatgccct tccatgtctt gaaagattga    2042
ttttaagaga ttgtaagagt ttagaagaga ttcatccatc aattggacat cacaaaaggc    2102
ttgtttacgt gagtgtgagc tactgttcaa gccttaaaag ctttccaccc atcatacaga    2162
tgcaaatgtt gaagactctt attctctctt attgctatca acttcaacag tttccggata    2222
tccagtcgaa caagagtcta ccaaatttga aaattcttaa tcttgaacaa tgtggaaacc    2282
taatcacgac accagatttt gaaggcttc catgtcttga aagattgatt ttatcacatt    2342
gtatgagttt agaagagatt catccatcaa ttggatatca caaaggcttt gttttcgtga    2402
acctgaactg gtgtagagca cttaaaaggt ttccacccat catacagatg gaaaaattgg    2462
agactcttat tctctcttat tgcgagcaac tacaacagtt tccggatatc cagtcgaaca    2522
tggatagctt ggtaacccttt gatttgagtg atactggtat agaaataatc ctaccgtcag    2582
ctggacgact cccaggtctc aagtatctca atctgtcata ctgcataaac cttgtagaat    2642
tgccagacct cccatcaagc atagctattc tcagagcaga tggttgtgac tcacttgaaa    2702
ttgtaagaga tttatcagac tataaatggt tgtggaaagt ctctctttgg aggagagcga    2762
ataagagggt actactttct atgcttgagg aaaatgcagt taagaagat cgctttatga    2822 gtgtcttact tcccgcgcct gaaccatcaa gcatttatac caaacttgtc acattgcaac    2882
ttccacacaa ctggtacagt gactttagtg gattttttatt atcattacgt gctcctgatt    2942
cccaatccga tacgtatcgc atagttatta agcaggagat gtccacggat caccctgaag    3002
agttcagtga aaattggaaa aattttgacc atgaaagggt gggttatgta ccctttaatt    3062
tattgaggca catcccatgg ttcaatccta catacactaa agtatttca tttaagatgg    3122 gtgatgcttg tcttaatgta gaacttgttc gtaggaaaag taaataggt gatttaaacg    3182 aacacctaat cgattactta gagtgttggg atgaagaata tgaagataaa aagacatttg    3242
agatcacaaa tgatgcaacg tcttctgaaa ttcagatttt atggagacat cggtagtcga    3302
tctcagtttc aaatttcaac atttgcccac attttgttac catttaagt ttgttttac    3362 ttctccaaca tcattgcaac ctaaaagaag ttgtaataat ttttcctcta ttatctctta    3422
agacntcaca ttcaaaaaaa aaaaaaaaaa aaaa                              3456
```

<210> SEQ ID NO 13
<211> LENGTH: 476
<212> TYPE: PRT
<213> ORGANISM: Helianthus annuus

<400> SEQUENCE: 13

```
Met Ala Val Gly Leu Met Glu Thr Leu Lys Glu Ala Ile Thr Ala Tyr
 1               5                   10                  15

Thr Gly Leu Ser Pro Thr Thr Phe Phe Thr Val Leu Ala Ala Gly Val
             20                  25                  30
```

```
Thr Val Tyr Tyr Ile Val Ser Val Leu Phe Met Arg Gly Ser Ser Asp
         35                  40                  45

His His Gln Gln His Ser Gln Met Ser Glu Glu Asp Arg Ser Ala
 50                  55                  60

Ala Ser Ser Ser Ala Ser His Ser Ile Ser Ala Ser Thr Ser Gln
 65                  70                  75                  80

Ser Trp Asn His Asp Val Phe Leu Ser Phe Arg Gly Glu Asp Thr Arg
                 85                  90                  95

Asn Ser Phe Val Asp His Leu Tyr Ala Ala Leu Ala Gln Gln Gly Ile
             100                 105                 110

Gln Ala Tyr Lys Asp Asp Glu Thr Leu Pro Arg Gly Glu Arg Ile Gly
             115                 120                 125

Pro Ala Leu Leu Lys Ala Ile Gln Glu Ser Arg Ile Ala Val Val Val
         130                 135                 140

Phe Ser Gln Asn Tyr Ala Asp Ser Ser Trp Cys Leu Asp Glu Leu Ala
145                 150                 155                 160

His Ile Met Glu Cys Met Asp Thr Arg Gly Gln Ile Val Ile Pro Ile
                 165                 170                 175

Phe Tyr Phe Val Asp Pro Ser Asp Val Arg Lys Gln Lys Gly Lys Tyr
             180                 185                 190

Gly Lys Ala Phe Arg Lys Arg Lys Glu Asn Arg Gln Lys Val Glu
             195                 200                 205

Ser Trp Arg Lys Ala Leu Glu Lys Ala Gly Asn Leu Ser Gly Trp Val
         210                 215                 220

Ile Asn Glu Asn Ser His Glu Ala Lys Cys Ile Lys Glu Ile Val Ala
225                 230                 235                 240

Thr Ile Ser Ser Arg Leu Pro Thr Leu Ser Thr Asn Val Asn Lys Asp
                 245                 250                 255

Leu Ile Gly Ile Glu Thr Arg Leu Gln Asp Leu Lys Ser Lys Leu Lys
             260                 265                 270

Met Glu Ser Gly Asp Val Arg Ile Ile Gly Ile Trp Gly Val Gly Gly
         275                 280                 285

Gly Gly Lys Thr Thr Leu Ala Ser Ala Ala Tyr Ala Glu Ile Ser Arg
290                 295                 300

Arg Phe Glu Ala His Cys Leu Leu Gln Asn Ile Arg Glu Glu Ser Asn
305                 310                 315                 320

Lys His Gly Leu Glu Lys Leu Gln Glu Lys Ile Leu Ser Leu Val Leu
                 325                 330                 335

Lys Thr Lys Asp Val Val Gly Ser Glu Ile Glu Gly Arg Ser Met
             340                 345                 350

Ile Glu Arg Arg Leu Arg Asn Lys Ser Val Leu Val Leu Asp Asp
             355                 360                 365

Val Asp Asp Leu Lys Gln Leu Glu Ala Leu Ala Gly Ser His Ala Trp
         370                 375                 380

Phe Gly Lys Gly Ser Arg Ile Ile Ile Thr Thr Arg Asp Glu His Leu
385                 390                 395                 400

Leu Thr Arg His Ala Asp Met Ile Tyr Glu Val Ser Leu Leu Ser His
                 405                 410                 415

Asp Glu Ala Met Glu Leu Phe Asn Lys His Ala Tyr Arg Lys Asp Lys
             420                 425                 430

Pro Ile Glu Asp Tyr Glu Met Leu Ser Asn Asp Val Val Ser Tyr Ala
             435                 440                 445
```

Ser Gly Leu Pro Leu Ala Leu Glu Ile Leu Gly Ser Phe Leu Tyr Asp
    450                 455                 460

Lys Asn Lys Asp Glu Trp Lys Ser Ala Leu Ala Ser
465                 470                 475

<210> SEQ ID NO 14
<211> LENGTH: 1360
<212> TYPE: DNA
<213> ORGANISM: Helianthus annuus

<400> SEQUENCE: 14

```
ggcacgagtg aacaatggct gttggactta tggagactct gaaagaagct ataaccgcct    60
acaccggact ctctcccact actttcttca ctgttctcgc cgccggtgtc accgtctact   120
acatcgtttc cgttctgttc atgagaggct cctccgatca ccatcaacaa cacagccaaa   180
tgtcttccga agaagacaga tcagcggcat cttcttcgtc cgcttctcac tcaatttctg   240
cctctacttc tcaatcatgg aatcatgatg tatttctgag ctttcgggga aagacaccc    300
gtaatagctt tgtggatcat ctctatgcgg ctcttgcaca acaaggaatc caggcgtaca   360
aggatgacga aacacttcct cggggtgagc gaatcggtcc agccctcttg aaagctatcc   420
aagaatcacg catcgccgtt gttgtgttct ctcaaaacta tgcggattca tcttggtgct   480
tggacgagct tgcacatatt atggagtgca tggacacgag agggcagatc gtgattccca   540
tattttattt tgtagatcca tcggatgtta gaaaacaaaa ggggaaatat ggaaaagcat   600
ttagaaaacg taagagggaa ataggcaaaa agttgaatc atggagaaaa gctctggaaa   660
aggctggcaa tctttctgga tgggtcatca atgaaaacag tcacgaagca aaatgcatca   720
aagaaattgt tgctacaatt tctagtaggc tgcctacact aagtacaaac gtcaataaag   780
acctcattgg aatagagaca cgcttacaag atctgaaatc aaagttgaaa atggagtcag   840
gtgatgtacg cattattgga atatggggag ttggggggtgg tggtaagact actctcgcat   900
ctgctgctta tgcggaaatc tctcgccgat ttgaagctca ctgccttctt caaaatatcc   960
gtgaggagtc aaacaagcat ggtttggaaa aactacaaga aaaaattctc tcacttgttt  1020
tgaaaacaaa agatgttgtg gtagggagtg agatagaagg aagaagcatg atagaaagaa  1080
ggttacgtaa taaaagcgta ttagttgttc ttgacgatgt tgatgacctc aagcaactag  1140
aggctctagc cggatcacat gcttggtttg gtaaggggag caggataata attacgacga  1200
gggatgagca tttgctaacc cgccatgcag acatgatata tgaagtgagt ttgttatcac  1260
atgacgaggc tatggagctc ttcaacaaac atgcatatcg gaaagataaa cctatagaag  1320
attacgagat gctttcaaac gatgtagttt cttatgctag                        1360
```

<210> SEQ ID NO 15
<211> LENGTH: 20
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (1)...(20)
<223> OTHER INFORMATION: n = A,T,C or G
<220> FEATURE:
<221> NAME/KEY: misc_feature
<222> LOCATION: 3, 6, 9, 12, 15, 18
<223> OTHER INFORMATION: n = A,T,C or G
<220> FEATURE:
<221> NAME/KEY: misc_feature
<222> LOCATION: 3, 6, 9, 12, 15, 18
<223> OTHER INFORMATION: n = A,T,C or G

<400> SEQUENCE: 15
ggnggnrtng gnaanacnac                                               20

<210> SEQ ID NO 16
<211> LENGTH: 17
<212> TYPE: DNA
<213> ORGANISM: Artificial Sequence
<220> FEATURE:
<221> NAME/KEY: misc_feature
<222> LOCATION: (1)...(17)
<223> OTHER INFORMATION: n = A,T,C or G
<220> FEATURE:
<221> NAME/KEY: misc_feature
<222> LOCATION: 3, 6, 9, 12, 15
<223> OTHER INFORMATION: Oligonucleotide primer
<220> FEATURE:
<221> NAME/KEY: misc_feature
<222> LOCATION: 3, 6, 9, 12, 15
<223> OTHER INFORMATION: n = A,T,C or G
<220> FEATURE:
<223> OTHER INFORMATION: n = A,T,C or G

<400> SEQUENCE: 16
agngynagng gnagncc                                                  17

<210> SEQ ID NO 17
<211> LENGTH: 17
<212> TYPE: DNA
<213> ORGANISM: Artificial Sequence
<220> FEATURE:
<221> NAME/KEY: misc_feature
<222> LOCATION: (1)...(17)
<223> OTHER INFORMATION: n = A,T,C or G
<220> FEATURE:
<221> NAME/KEY: misc_feature
<222> LOCATION: 3, 6, 9, 12, 15
<223> OTHER INFORMATION: Oligonucleotide primer
<220> FEATURE:
<221> NAME/KEY: misc_feature
<222> LOCATION: 3, 6, 9, 12, 15
<223> OTHER INFORMATION: n = A,T,C or G
<220> FEATURE:
<223> OTHER INFORMATION: n = A,T,C or G

<400> SEQUENCE: 17
agngynagng gnaancc                                                  17

<210> SEQ ID NO 18
<211> LENGTH: 17
<212> TYPE: DNA
<213> ORGANISM: Artificial Sequence
<220> FEATURE:
<221> NAME/KEY: misc_feature
<222> LOCATION: (1)...(17)
<223> OTHER INFORMATION: n = A,T,C or G
<220> FEATURE:
<221> NAME/KEY: misc_feature
<222> LOCATION: 3, 6, 9, 12, 15
<223> OTHER INFORMATION: Oligonucleotide primer
<220> FEATURE:
<221> NAME/KEY: misc_feature
<222> LOCATION: 3, 6, 9, 12, 15
<223> OTHER INFORMATION: n = A,T,C or G
<220> FEATURE:
<223> OTHER INFORMATION: n = A,T,C or G

<400> SEQUENCE: 18
agngynaang gnagncc                                                  17

<210> SEQ ID NO 19

```
<211> LENGTH: 17
<212> TYPE: DNA
<213> ORGANISM: Artificial Sequence
<220> FEATURE:
<221> NAME/KEY: misc_feature
<222> LOCATION: (1)...(17)
<223> OTHER INFORMATION: n = A,T,C or G
<220> FEATURE:
<221> NAME/KEY: misc_feature
<222> LOCATION: 3, 6, 9, 12, 15
<223> OTHER INFORMATION: Oligonucleotide primer
<220> FEATURE:
<221> NAME/KEY: misc_feature
<222> LOCATION: 3, 6, 9, 12, 15
<223> OTHER INFORMATION: n = A,T,C or G
<220> FEATURE:
<223> OTHER INFORMATION: n = A,T,C or G

<400> SEQUENCE: 19
agngynaang gnaancc                                                 17

<210> SEQ ID NO 20
<211> LENGTH: 17
<212> TYPE: DNA
<213> ORGANISM: Artificial Sequence
<220> FEATURE:
<221> NAME/KEY: misc_feature
<222> LOCATION: (1)...(17)
<223> OTHER INFORMATION: n = A,T,C or G
<220> FEATURE:
<221> NAME/KEY: misc_feature
<222> LOCATION: 3, 6, 9, 12, 15
<223> OTHER INFORMATION: Oligonucleotide primer
<220> FEATURE:
<221> NAME/KEY: misc_feature
<222> LOCATION: 3, 6, 9, 12, 15
<223> OTHER INFORMATION: n = A,T,C or G
<220> FEATURE:
<223> OTHER INFORMATION: n = A,T,C or G

<400> SEQUENCE: 20
aangynagng gnagncc                                                 17

<210> SEQ ID NO 21
<211> LENGTH: 17
<212> TYPE: DNA
<213> ORGANISM: Artificial Sequence
<220> FEATURE:
<221> NAME/KEY: misc_feature
<222> LOCATION: (1)...(17)
<223> OTHER INFORMATION: n = A,T,C or G
<220> FEATURE:
<221> NAME/KEY: misc_feature
<222> LOCATION: 3, 6, 9, 12, 15
<223> OTHER INFORMATION: Oligonucleotide primer
<220> FEATURE:
<221> NAME/KEY: misc_feature
<222> LOCATION: 3, 6, 9, 12, 15
<223> OTHER INFORMATION: n = A,T,C or G
<220> FEATURE:
<223> OTHER INFORMATION: n = A,T,C or G

<400> SEQUENCE: 21
aangynagng gnaancc                                                 17

<210> SEQ ID NO 22
<211> LENGTH: 17
<212> TYPE: DNA
<213> ORGANISM: Artificial Sequence
<220> FEATURE:
<221> NAME/KEY: misc_feature
<222> LOCATION: (1)...(17)
<223> OTHER INFORMATION: n = A,T,C or G
```

```
<220> FEATURE:
<221> NAME/KEY: misc_feature
<222> LOCATION: 3, 6, 9, 12, 15
<223> OTHER INFORMATION: Oligonucleotide primer
<220> FEATURE:
<221> NAME/KEY: misc_feature
<222> LOCATION: 3, 6, 9, 12, 15
<223> OTHER INFORMATION: n = A,T,C or G
<220> FEATURE:
<223> OTHER INFORMATION: n = A,T,C or G

<400> SEQUENCE: 22
aangynaang gnagncc                                                    17

<210> SEQ ID NO 23
<211> LENGTH: 17
<212> TYPE: DNA
<213> ORGANISM: Artificial Sequence
<220> FEATURE:
<221> NAME/KEY: misc_feature
<222> LOCATION: (1)...(17)
<223> OTHER INFORMATION: n = A,T,C or G
<220> FEATURE:
<221> NAME/KEY: misc_feature
<222> LOCATION: 3, 6, 9, 12, 15
<223> OTHER INFORMATION: Oligonucleotide primer
<220> FEATURE:
<221> NAME/KEY: misc_feature
<222> LOCATION: 3, 6, 9, 12, 15
<223> OTHER INFORMATION: n = A,T,C or G
<220> FEATURE:
<223> OTHER INFORMATION: n = A,T,C or G

<400> SEQUENCE: 23
aangynaang gnaancc                                                    17

<210> SEQ ID NO 24
<211> LENGTH: 20
<212> TYPE: DNA
<213> ORGANISM: Artificial Sequence
<220> FEATURE:
<221> NAME/KEY: misc_feature
<222> LOCATION: (1)...(20)
<223> OTHER INFORMATION: n = A,T,C or G
<220> FEATURE:
<221> NAME/KEY: misc_feature
<222> LOCATION: 3, 9, 12, 15
<223> OTHER INFORMATION: Oligonucleotide primer
<220> FEATURE:
<221> NAME/KEY: misc_feature
<222> LOCATION: 3, 9, 12, 15
<223> OTHER INFORMATION: n = A,T,C or G
<220> FEATURE:
<223> OTHER INFORMATION: n = A,T,C or G

<400> SEQUENCE: 24
ggnttyggnr angtntayaa                                                 20

<210> SEQ ID NO 25
<211> LENGTH: 20
<212> TYPE: DNA
<213> ORGANISM: Artificial Sequence
<220> FEATURE:
<221> NAME/KEY: misc_feature
<222> LOCATION: (1)...(20)
<223> OTHER INFORMATION: n = A,T,C or G
<220> FEATURE:
<221> NAME/KEY: misc_feature
<222> LOCATION: 3, 9, 12, 15
<223> OTHER INFORMATION: Oligonucleotide primer
<220> FEATURE:
<221> NAME/KEY: misc_feature
<222> LOCATION: 3, 9, 12, 15
```

```
<223> OTHER INFORMATION: n = A,T,C or G
<220> FEATURE:
<223> OTHER INFORMATION: n = A,T,C or G

<400> SEQUENCE: 25
ggnttyggnr angtntayag                                               20

<210> SEQ ID NO 26
<211> LENGTH: 17
<212> TYPE: DNA
<213> ORGANISM: Artificial Sequence
<220> FEATURE:
<221> NAME/KEY: misc_feature
<222> LOCATION: (1)...(17)
<223> OTHER INFORMATION: n = A,T,C or G
<220> FEATURE:
<221> NAME/KEY: misc_feature
<222> LOCATION: 3, 6, 9, 12, 15
<223> OTHER INFORMATION: Oligonucleotide primer
<220> FEATURE:
<221> NAME/KEY: misc_feature
<222> LOCATION: 3, 6, 9, 12, 15
<223> OTHER INFORMATION: n = A,T,C or G
<220> FEATURE:
<223> OTHER INFORMATION: n = A,T,C or G

<400> SEQUENCE: 26
trnccnykng cngcncc                                                  17

<210> SEQ ID NO 27
<211> LENGTH: 17
<212> TYPE: DNA
<213> ORGANISM: Artificial Sequence
<220> FEATURE:
<221> NAME/KEY: misc_feature
<222> LOCATION: (1)...(17)
<223> OTHER INFORMATION: n = A,T,C or G
<220> FEATURE:
<221> NAME/KEY: misc_feature
<222> LOCATION: 6, 12
<223> OTHER INFORMATION: Oligonucleotide primer
<220> FEATURE:
<221> NAME/KEY: misc_feature
<222> LOCATION: 6, 12
<223> OTHER INFORMATION: n = A,T,C or G
<220> FEATURE:
<223> OTHER INFORMATION: n = A,T,C or G

<400> SEQUENCE: 27
ccraansyrt anacrtc                                                  17

<210> SEQ ID NO 28
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 28
cgatgtgaag gtagggaatg ag                                            22

<210> SEQ ID NO 29
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 29
gggagtgaga taataggaag gagc                                          24
```

<210> SEQ ID NO 30
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 30
ggtagggagt gagatagaag gaag                                    24

<210> SEQ ID NO 31
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 31
tatgaagtga atttgttatc aca                                     23

<210> SEQ ID NO 32
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 32
tatgaagtga gtttgttatc aca                                     23

<210> SEQ ID NO 33
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 33
aagacgactc tcgcatctgc tgccta                                  26

<210> SEQ ID NO 34
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 34
gaagacgact ctcgcatctg ctgctt                                  26

<210> SEQ ID NO 35
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 35
gccaccagca taagaaacta cc                                      22

<210> SEQ ID NO 36
<211> LENGTH: 22
<212> TYPE: DNA
<213> ORGANISM: Artificial Sequence
<220> FEATURE:

<223> OTHER INFORMATION: Oligonucleotide primer

<400> SEQUENCE: 36
ggccgtcagc ataagaaact ac        22

<210> SEQ ID NO 37
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 37
ggaggccact agcataagaa ac        22

<210> SEQ ID NO 38
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 38
ggggaggcca ccagcataag aaacta        26

<210> SEQ ID NO 39
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 39
cgaaggggag gccactagca taagaa        26

<210> SEQ ID NO 40
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 40
caattattat ccggctcccc tcacca        26

<210> SEQ ID NO 41
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 41
tcttatatcg tgtctgcatg gcgggt        26

<210> SEQ ID NO 42
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 42
cacttcataa atcgtttgcg ccctgc        26

```
<210> SEQ ID NO 43
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 43
gcagcggtca gattgtagct gtcaaa                                    26

<210> SEQ ID NO 44
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 44
gccagccgct atcttcattc ttgtgt                                    26

<210> SEQ ID NO 45
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 45
ggataggaac gggctgcagg gtaac                                     25

<210> SEQ ID NO 46
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 46
tttggtcacc atcagcacag tatccg                                    26

<210> SEQ ID NO 47
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 47
cttgggtttg gggaggtgta cagagg                                    26

<210> SEQ ID NO 48
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 48
cttggatgct gcaattaagc gactgg                                    26

<210> SEQ ID NO 49
<211> LENGTH: 25
<212> TYPE: DNA
<213> ORGANISM: Artificial Sequence
<220> FEATURE:
<223> OTHER INFORMATION: Oligonucleotide primer
```

<400> SEQUENCE: 49
ggcggcgcct atgcatattt tgagt                                         25

<210> SEQ ID NO 50
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 50
cttcaaaacc ggggtctgga gtcgtt                                        26

<210> SEQ ID NO 51
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 51
cggagactcc atgttagcgg ttgaaa                                        26

<210> SEQ ID NO 52
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 52
aactatgtct ttccatacca gtcacccgg                                     29

<210> SEQ ID NO 53
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 53
tcggagactc catgttagcg gttgaa                                        26

<210> SEQ ID NO 54
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 54
gaccgttcct tcaattaatg ggttgc                                        26

<210> SEQ ID NO 55
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 55
gcgattaagt tgggtaacgc cagggt                                        26

<210> SEQ ID NO 56
<211> LENGTH: 26

<212> TYPE: DNA
<213> ORGANISM: Artificial Sequence
<220> FEATURE:
<223> OTHER INFORMATION: Oligonucleotide primer

<400> SEQUENCE: 56
tccggctcgt atgttgtgtg gaattg                                              26

<210> SEQ ID NO 57
<211> LENGTH: 389
<212> TYPE: PRT
<213> ORGANISM: Arabidopsis thaliana

<400> SEQUENCE: 57

Met Gly Gly Cys Phe Ser Asn Arg Ile Lys Thr Asp Ile Ala Ser Ser
 1               5                  10                  15

Thr Trp Leu Ser Ser Lys Phe Leu Ser Arg Asp Gly Ser Lys Gly Ser
             20                  25                  30

Ser Thr Ala Ser Phe Ser Tyr Met Pro Arg Thr Glu Gly Glu Ile Leu
         35                  40                  45

Gln Asn Ala Asn Leu Lys Asn Phe Ser Leu Ser Glu Leu Lys Ser Ala
     50                  55                  60

Thr Arg Asn Phe Arg Pro Asp Ser Val Val Gly Glu Gly Gly Phe Gly
 65                  70                  75                  80

Cys Val Phe Lys Gly Trp Ile Asp Glu Ser Ser Leu Ala Pro Ser Lys
                 85                  90                  95

Pro Gly Thr Gly Ile Val Ile Ala Val Lys Arg Leu Asn Gln Glu Gly
            100                 105                 110

Phe Gln Gly His Arg Glu Trp Leu Ala Glu Ile Asn Tyr Leu Gly Gln
        115                 120                 125

Leu Asp His Pro Asn Leu Val Lys Leu Ile Gly Tyr Cys Leu Glu Glu
    130                 135                 140

Glu His Arg Leu Leu Val Tyr Glu Phe Met Thr Arg Gly Ser Leu Glu
145                 150                 155                 160

Asn His Leu Phe Arg Arg Gly Thr Phe Tyr Gln Pro Leu Ser Trp Asn
                165                 170                 175

Thr Arg Val Arg Met Ala Leu Gly Ala Ala Arg Gly Leu Ala Phe Leu
            180                 185                 190

His Asn Ala Gln Pro Gln Val Ile Tyr Arg Asp Phe Lys Ala Ser Asn
        195                 200                 205

Ile Leu Leu Asp Ser Asn Tyr Asn Ala Lys Leu Ser Asp Phe Gly Leu
    210                 215                 220

Ala Arg Asp Gly Pro Met Gly Asp Asn Ser His Val Ser Thr Arg Val
225                 230                 235                 240

Met Gly Thr Gln Gly Tyr Ala Ala Pro Glu Tyr Leu Ala Thr Gly His
                245                 250                 255

Leu Ser Val Lys Ser Asp Val Tyr Ser Phe Gly Val Val Leu Leu Glu
            260                 265                 270

Leu Leu Ser Gly Arg Arg Ala Ile Asp Lys Asn Gln Pro Val Val Glu
        275                 280                 285

His Asn Leu Val Asp Trp Ala Arg Pro Tyr Leu Thr Asn Lys Arg Arg
    290                 295                 300

Leu Leu Arg Val Met Asp Pro Arg Leu Gln Gly Gln Tyr Ser Leu Thr
305                 310                 315                 320

Arg Ala Leu Lys Ile Ala Val Leu Ala Leu Asp Cys Ile Ser Ile Asp
                325                 330                 335

-continued

```
Ala Lys Ser Arg Pro Thr Met Asn Glu Ile Val Lys Thr Met Glu Glu
                340                 345                 350

Leu His Ile Gln Lys Glu Ala Ser Lys Glu Gln Gln Asn Pro Gln Ile
            355                 360                 365

Ser Ile Asp Asn Ile Ile Asn Lys Ser Pro Gln Ala Val Asn Tyr Pro
            370                 375                 380

Arg Pro Ser Ile Met
385

<210> SEQ ID NO 58
<211> LENGTH: 410
<212> TYPE: PRT
<213> ORGANISM: Arabidopsis thaliana

<400> SEQUENCE: 58

Met Gly Ile Cys Leu Ser Ala Gln Val Lys Ala Glu Ser Ser Gly Ala
 1               5                  10                  15

Ser Thr Lys Tyr Asp Ala Lys Asp Ile Gly Ser Leu Gly Ser Lys Ala
             20                  25                  30

Ser Ser Val Ser Val Arg Pro Ser Pro Arg Thr Glu Gly Glu Ile Leu
         35                  40                  45

Gln Ser Pro Asn Leu Lys Ser Phe Ser Phe Ala Glu Leu Lys Ser Ala
     50                  55                  60

Thr Arg Asn Phe Arg Pro Asp Ser Val Leu Gly Glu Gly Gly Phe Gly
 65                  70                  75                  80

Cys Val Phe Lys Gly Trp Ile Asp Glu Lys Ser Leu Thr Ala Ser Arg
                 85                  90                  95

Pro Gly Thr Gly Leu Val Ile Ala Val Lys Lys Leu Asn Gln Asp Gly
            100                 105                 110

Trp Gln Gly His Gln Glu Trp Leu Ala Glu Val Asn Tyr Leu Gly Gln
        115                 120                 125

Phe Ser His Arg His Leu Val Lys Leu Ile Gly Tyr Cys Leu Glu Asp
    130                 135                 140

Glu His Arg Leu Leu Val Tyr Glu Phe Met Pro Arg Gly Ser Leu Glu
145                 150                 155                 160

Asn His Leu Phe Arg Arg Gly Leu Tyr Phe Gln Pro Leu Ser Trp Lys
                165                 170                 175

Leu Arg Leu Lys Val Ala Leu Gly Ala Ala Lys Gly Leu Ala Phe Leu
            180                 185                 190

His Ser Ser Glu Thr Arg Val Ile Tyr Arg Asp Phe Lys Thr Ser Asn
        195                 200                 205

Ile Leu Leu Asp Ser Glu Tyr Asn Ala Lys Leu Ser Asp Phe Gly Leu
    210                 215                 220

Ala Lys Asp Gly Pro Ile Gly Asp Lys Ser His Val Ser Thr Arg Val
225                 230                 235                 240

Met Gly Thr His Gly Tyr Ala Ala Pro Glu Tyr Leu Ala Thr Gly His
                245                 250                 255

Leu Thr Thr Lys Ser Asp Val Tyr Ser Phe Gly Val Val Leu Leu Glu
            260                 265                 270

Leu Leu Ser Gly Arg Arg Ala Val Asp Lys Asn Arg Pro Ser Gly Glu
        275                 280                 285

Arg Asn Leu Val Glu Trp Ala Lys Pro Tyr Leu Val Asn Lys Arg Lys
    290                 295                 300

Ile Phe Arg Val Ile Asp Asn Arg Leu Gln Asp Gln Tyr Ser Met Glu
```

```
305                 310                 315                 320
Glu Ala Cys Lys Val Ala Thr Leu Ser Leu Arg Cys Leu Thr Thr Glu
                325                 330                 335

Ile Lys Leu Arg Pro Asn Met Ser Glu Val Val Ser His Leu Glu His
                340                 345                 350

Ile Gln Ser Leu Asn Ala Ala Ile Gly Gly Asn Met Asp Lys Thr Asp
                355                 360                 365

Arg Arg Met Arg Arg Ser Asp Ser Val Val Ser Lys Lys Val Asn
                370                 375                 380

Ala Gly Phe Ala Arg Gln Thr Ala Val Gly Ser Thr Val Val Ala Tyr
385                 390                 395                 400

Pro Arg Pro Ser Ala Ser Pro Leu Tyr Val
                405                 410

<210> SEQ ID NO 59
<211> LENGTH: 426
<212> TYPE: PRT
<213> ORGANISM: Arabidopsis thaliana

<400> SEQUENCE: 59

Met Gly Asn Cys Leu Asp Ser Ser Ala Lys Val Asp Ser Ser His
1               5                   10                  15

Ser Pro His Ala Asn Ser Ala Ser Leu Ser Ser Arg Val Ser Ser Lys
                20                  25                  30

Thr Ser Arg Ser Thr Val Pro Ser Ser Leu Ser Ile Asn Ser Tyr Ser
            35                  40                  45

Ser Val Glu Ser Leu Pro Thr Pro Arg Thr Glu Gly Glu Ile Leu Ser
        50                  55                  60

Ser Pro Asn Leu Lys Ala Phe Thr Phe Asn Glu Leu Lys Asn Ala Thr
65                  70                  75                  80

Arg Asn Phe Arg Pro Asp Ser Leu Leu Gly Glu Gly Gly Phe Gly Tyr
                85                  90                  95

Val Phe Lys Gly Trp Ile Asp Gly Thr Thr Leu Thr Ala Ser Lys Pro
                100                 105                 110

Gly Ser Gly Ile Val Val Ala Val Lys Lys Leu Lys Thr Glu Gly Tyr
            115                 120                 125

Gln Gly His Lys Glu Trp Leu Thr Glu Val Asn Tyr Leu Gly Gln Leu
        130                 135                 140

Ser His Pro Asn Leu Val Lys Leu Val Gly Tyr Cys Val Glu Gly Glu
145                 150                 155                 160

Asn Arg Leu Leu Val Tyr Glu Phe Met Pro Lys Gly Ser Leu Glu Asn
                165                 170                 175

His Leu Phe Arg Arg Gly Ala Gln Pro Leu Thr Trp Ala Ile Arg Met
                180                 185                 190

Lys Val Ala Ile Gly Ala Ala Lys Gly Leu Thr Phe Leu His Asp Ala
            195                 200                 205

Lys Ser Gln Val Ile Tyr Arg Asp Phe Lys Ala Ala Asn Ile Leu Leu
        210                 215                 220

Asp Ala Glu Phe Asn Ser Lys Leu Ser Asp Phe Gly Leu Ala Lys Ala
225                 230                 235                 240

Gly Pro Thr Gly Asp Lys Thr His Val Ser Thr Gln Val Met Gly Thr
                245                 250                 255

His Gly Tyr Ala Ala Pro Glu Tyr Val Ala Thr Gly Arg Leu Thr Ala
                260                 265                 270
```

```
Lys Ser Asp Val Tyr Ser Phe Gly Val Val Leu Glu Leu Leu Ser
        275                 280                 285

Gly Arg Arg Ala Val Asp Lys Ser Lys Val Gly Met Glu Gln Ser Leu
        290                 295                 300

Val Asp Trp Ala Thr Pro Tyr Leu Gly Asp Lys Arg Lys Leu Phe Arg
305                 310                 315                 320

Ile Met Asp Thr Arg Leu Gly Gly Gln Tyr Pro Gln Lys Gly Ala Tyr
                    325                 330                 335

Thr Ala Ala Ser Leu Ala Leu Gln Cys Leu Asn Pro Asp Ala Lys Leu
                340                 345                 350

Arg Pro Lys Met Ser Glu Val Leu Ala Lys Leu Asp Gln Leu Glu Ser
            355                 360                 365

Thr Lys Pro Gly Thr Gly Val Gly Asn Arg Gln Ala Gln Ile Asp Ser
        370                 375                 380

Pro Arg Gly Ser Asn Gly Ser Ile Val Gln Lys Ser Pro Arg Arg Tyr
385                 390                 395                 400

Ser Tyr Asp Arg Pro Leu Leu His Ile Thr Pro Gly Ala Ser Pro Leu
                    405                 410                 415

Pro Thr His Asn His Ser Pro Arg Val Arg
                420                 425

<210> SEQ ID NO 60
<211> LENGTH: 370
<212> TYPE: PRT
<213> ORGANISM: Lycopersicon esculentum

<400> SEQUENCE: 60

Met Ser Cys Phe Ser Cys Cys Asp Asp Asp Met His Arg Ala Thr
1               5                   10                  15

Asp Asn Gly Pro Phe Met Ala His Asn Ser Ala Gly Asn Asn Gly Gly
                20                  25                  30

Gln Arg Ala Thr Glu Ser Ala Gln Arg Glu Thr Gln Thr Val Asn Ile
            35                  40                  45

Gln Pro Ile Ala Val Pro Ser Ile Ala Val Asp Glu Leu Lys Asp Ile
        50                  55                  60

Thr Asp Asn Phe Gly Ser Lys Ala Leu Ile Gly Glu Gly Ser Tyr Gly
65                  70                  75                  80

Arg Val Tyr His Gly Val Leu Lys Ser Gly Arg Ala Ala Ile Lys
                    85                  90                  95

Lys Leu Asp Ser Ser Lys Gln Pro Asp Arg Glu Phe Leu Ala Gln Val
                100                 105                 110

Ser Met Val Ser Arg Leu Lys Asp Glu Asn Val Val Glu Leu Leu Gly
            115                 120                 125

Tyr Cys Val Asp Gly Gly Phe Arg Val Leu Ala Tyr Glu Tyr Ala Pro
        130                 135                 140

Asn Gly Ser Leu His Asp Ile Leu His Gly Arg Lys Gly Val Lys Gly
145                 150                 155                 160

Ala Gln Pro Gly Pro Val Leu Ser Trp Ala Gln Arg Val Lys Ile Ala
                    165                 170                 175

Val Gly Ala Ala Lys Gly Leu Glu Tyr Leu His Glu Lys Ala Gln Pro
                180                 185                 190

His Ile Ile His Arg Asp Ile Lys Ser Ser Asn Ile Leu Leu Phe Asp
            195                 200                 205

Asp Asp Val Ala Lys Ile Ala Asp Phe Asp Leu Ser Asn Gln Ala Pro
        210                 215                 220
```

Asp Met Ala Ala Arg Leu His Ser Thr Arg Val Leu Gly Thr Phe Gly
225                 230                 235                 240

Tyr His Ala Pro Glu Tyr Ala Met Thr Gly Gln Leu Ser Ser Lys Ser
            245                 250                 255

Asp Val Tyr Ser Phe Gly Val Val Leu Glu Leu Leu Thr Gly Arg
        260                 265                 270

Lys Pro Val Asp His Thr Leu Pro Arg Gly Asn Arg Val Cys Tyr Leu
            275                 280                 285

Gly Asn Ala Arg Leu Ser Glu Asp Lys Val Lys Gln Cys Val Asp Ala
        290                 295                 300

Arg Leu Asn Thr Asp Tyr Pro Pro Lys Ala Ile Ala Lys Met Ala Ala
305                 310                 315                 320

Val Ala Ala Leu Cys Val Gln Tyr Glu Ala Asp Phe Arg Pro Asn Met
            325                 330                 335

Ser Ile Val Val Lys Leu Phe Ser Leu Cys Cys Leu Asp Leu Tyr Gln
            340                 345                 350

Val Arg His Gln Ala Cys Glu Phe Ser Pro Tyr Pro Cys Leu Tyr Val
            355                 360                 365

Met Lys
    370

<210> SEQ ID NO 61
<211> LENGTH: 176
<212> TYPE: PRT
<213> ORGANISM: Nicotiana tabacum

<400> SEQUENCE: 61

Gly Met Gly Gly Val Gly Lys Thr Thr Ile Ala Arg Ala Ile Phe Asp
1               5                   10                  15

Thr Leu Leu Gly Arg Met Asp Ser Ser Tyr Gln Phe Asp Gly Ala Cys
            20                  25                  30

Phe Leu Lys Asp Ile Lys Glu Asn Lys Arg Gly Met His Ser Leu Gln
        35                  40                  45

Asn Ala Leu Leu Ser Glu Leu Leu Arg Glu Lys Ala Asn Tyr Asn Asn
    50                  55                  60

Glu Glu Asp Gly Lys His Gln Met Ala Ser Arg Leu Arg Ser Lys Lys
65                  70                  75                  80

Val Leu Ile Val Leu Asp Asp Ile Asp Asn Lys Asp His Tyr Leu Glu
                85                  90                  95

Tyr Leu Ala Gly Asp Leu Asp Trp Phe Gly Asn Gly Ser Arg Ile Ile
            100                 105                 110

Ile Thr Thr Arg Asp Lys His Leu Ile Glu Lys Asn Asp Ile Ile Tyr
        115                 120                 125

Glu Val Thr Ala Leu Pro Asp His Glu Ser Ile Gln Leu Phe Lys Gln
    130                 135                 140

His Ala Phe Gly Lys Glu Val Pro Asn Glu Asn Phe Glu Lys Leu Ser
145                 150                 155                 160

Leu Glu Val Val Asn Tyr Ala Lys Gly Leu Pro Leu Ala Leu Lys Val
                165                 170                 175

<210> SEQ ID NO 62
<211> LENGTH: 177
<212> TYPE: PRT
<213> ORGANISM: Linum usitatissimum

<400> SEQUENCE: 62

```
Gly Met Gly Gly Ile Gly Lys Thr Thr Thr Ala Lys Ala Val Tyr Asn
 1               5                  10                  15

Lys Ile Ser Ser His Phe Asp Arg Cys Cys Phe Val Asp Asn Val Arg
            20                  25                  30

Ala Met Gln Glu Gln Lys Asp Gly Ile Phe Ile Leu Gln Lys Lys Leu
            35                  40                  45

Val Ser Glu Ile Leu Arg Met Asp Ser Val Gly Phe Thr Asn Asp Ser
 50                  55                  60

Gly Gly Arg Lys Met Ile Lys Glu Arg Val Ser Lys Ser Lys Ile Leu
 65                  70                  75                  80

Val Val Leu Asp Asp Val Asp Glu Lys Phe Lys Phe Glu Asp Ile Leu
            85                  90                  95

Gly Cys Pro Lys Asp Phe Asp Ser Gly Thr Arg Phe Ile Ile Thr Ser
            100                 105                 110

Arg Asn Gln Asn Val Leu Ser Arg Leu Asn Glu Asn Gln Cys Lys Leu
            115                 120                 125

Tyr Glu Val Gly Ser Met Ser Glu Gln His Ser Leu Glu Leu Phe Ser
            130                 135                 140

Lys His Ala Phe Lys Lys Asn Thr Pro Pro Ser Asp Tyr Glu Thr Leu
145                 150                 155                 160

Ala Asn Asp Ile Val Ser Thr Thr Gly Gly Leu Pro Leu Thr Leu Lys
                    165                 170                 175

Val

<210> SEQ ID NO 63
<211> LENGTH: 165
<212> TYPE: PRT
<213> ORGANISM: Arabidopsis thaliana

<400> SEQUENCE: 63

Gly Met Ala Gly Ile Gly Lys Thr Thr Leu Ala Arg Ala Ala Tyr Asp
 1               5                  10                  15

Gln Leu Ser Arg Asp Phe Glu Ala Ser Cys Phe Ile Glu Asp Phe Asp
            20                  25                  30

Arg Glu Phe Gln Glu Lys Gly Phe Phe Gly Leu Leu Glu Lys Gln Leu
            35                  40                  45

Gly Val Asn Pro Gln Val Thr Arg Leu Ser Ile Leu Leu Lys Thr Leu
 50                  55                  60

Arg Ser Lys Arg Ile Leu Leu Val Leu Asp Asp Val Arg Lys Pro Leu
 65                  70                  75                  80

Gly Ala Thr Ser Phe Leu Cys Glu Phe Asp Trp Leu Gly Pro Gly Ser
            85                  90                  95

Leu Ile Ile Val Thr Ser Gln Asp Lys Gln Val Leu Val Gln Cys Gln
            100                 105                 110

Val Asn Glu Ile Tyr Lys Val Gln Gly Leu Asn Lys His Glu Ser Leu
            115                 120                 125

Gln Leu Phe Ser Arg Cys Ala Phe Gly Lys Asp Val Pro Asp Gln Asn
            130                 135                 140

Leu Leu Glu Leu Ser Met Lys Phe Val Asp Tyr Ala Asn Gly Asn Pro
145                 150                 155                 160

Leu Ala Leu Ser Ile
                165

<210> SEQ ID NO 64
```

-continued

```
<211> LENGTH: 173
<212> TYPE: PRT
<213> ORGANISM: Arabidopsis thaliana

<400> SEQUENCE: 64

Gly Pro Gly Gly Val Gly Lys Thr Thr Leu Met Gln Ser Ile Asn Asn
1               5                   10                  15

Glu Leu Ile Thr Lys Gly His Gln Tyr Asp Val Leu Ile Trp Val Gln
            20                  25                  30

Met Ser Arg Glu Phe Gly Glu Cys Thr Ile Gln Gln Ala Val Gly Ala
            35                  40                  45

Arg Leu Gly Leu Ser Trp Asp Glu Lys Glu Thr Gly Glu Asn Arg Ala
    50                  55                  60

Leu Lys Ile Tyr Arg Ala Leu Arg Gln Lys Arg Phe Leu Leu Leu Leu
65                  70                  75                  80

Asp Asp Val Trp Glu Glu Ile Asp Leu Glu Lys Thr Gly Val Pro Arg
                85                  90                  95

Pro Asp Arg Glu Asn Lys Cys Lys Val Met Phe Thr Thr Arg Ser Ile
            100                 105                 110

Ala Leu Cys Asn Asn Met Gly Ala Glu Tyr Lys Leu Arg Val Glu Phe
            115                 120                 125

Leu Glu Lys Lys His Ala Trp Glu Leu Phe Cys Ser Lys Val Trp Arg
        130                 135                 140

Lys Asp Leu Leu Glu Ser Ser Ser Ile Arg Arg Leu Ala Glu Ile Ile
145                 150                 155                 160

Val Ser Lys Cys Gly Gly Leu Pro Leu Ala Leu Ile Thr
                165                 170
```